(12) United States Patent
Chou et al.

(10) Patent No.: US 11,155,840 B2
(45) Date of Patent: Oct. 26, 2021

(54) HETEROLOGOUS EXPRESSION OF THERMOPHILIC LYSINE DECARBOXYLASE AND USES THEREOF

(71) Applicants: CATHAY BIOTECH INC., Shanghai (CN); CIBT America Inc., Newark, DE (US)

(72) Inventors: Howard Chou, Shanghai (CN); Xiucai Liu, Shanghai (CN)

(73) Assignees: CATHAY BIOTECH INC., Shanghai (CN); CIBT America Inc., Newark, DE (US)

(*) Notice: Subject to any disclaimer, the term of this patent is extended or adjusted under 35 U.S.C. 154(b) by 0 days.

(21) Appl. No.: 16/628,881

(22) PCT Filed: Jul. 6, 2017

(86) PCT No.: PCT/CN2017/091944
§ 371 (c)(1),
(2) Date: Jan. 6, 2020

(87) PCT Pub. No.: WO2019/006723
PCT Pub. Date: Jan. 10, 2019

(65) Prior Publication Data
US 2020/0224226 A1 Jul. 16, 2020

(51) Int. Cl.
| | | |
|---|---|---|
| *C12P 13/08* | (2006.01) |
| *C12P 13/00* | (2006.01) |
| *C12N 1/21* | (2006.01) |
| *C12N 9/88* | (2006.01) |
| *C12N 1/20* | (2006.01) |

(52) U.S. Cl.
CPC ............ *C12P 13/001* (2013.01); *C12N 1/20* (2013.01); *C12P 13/08* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 2011/0039313 A1 | 2/2011 | Verseck et al. | |
| 2012/0295317 A1 | 11/2012 | Schroder et al. | |
| 2018/0030430 A1* | 2/2018 | Lee | C12P 13/00 |

FOREIGN PATENT DOCUMENTS

| | | | | |
|---|---|---|---|---|
| CN | 101240258 A | 8/2008 | | |
| CN | 102753682 A | 10/2012 | | |
| EP | 0373962 B1 * | 9/1995 | ............... | C12N 9/93 |
| WO | WO-2008092720 A1 | 8/2008 | | |
| WO | WO-2016129812 A1 * | 8/2016 | ...... | C12Y 401/01018 |

OTHER PUBLICATIONS

Ninh et al., Appl. Enviromen. Microbiol. 79:1996-2001, 2013 (Year: 2013).*
Kwak et al., Biotechnol. Biofuels 10:20, 9 pages, Jan. 2017 (Year: 2017).*
UniProt Database Accession No. B9L088, Mar. 2016, 2 pages (Year: 2016).*
Wu et al., PLoS One 4:e4207, 2009, 15 pages (Year: 2009).*
International Search Report for Application No. PCT/CN2017/091944, dated Apr. 13, 2018.
Jianzhong Xu, "Breeding L-lysine hyperr producer by Corynebacterium glutamicum based on metabolic engineering," *Chinese Doctoral Dissertations Full-text Database (Basic Sciences)*, vol. 3, Mar. 15, 2015, Abstract only.
GenBank: GAQ24853, lysine decarboxylase [Tepidanaerobacter syntrophicus], Mar. 15, 2016.
GenBank: GAD14565, lysine decarboxylase [Geobacillus kaustophilus GBlys], Sep. 16, 2015.
GenBank: BAC09418, lysine decarboxylase [Thermosynechococcus elongatus BP-1], Oct. 7, 2016.
GenBank: ACM05730, lysine decarboxylase [Thermomicrobium roseum DSM 5159], Jan. 8, 2015.
Kanjee et al., "The Enzymatic Activities of the *Escherichia coli* Basic Aliphatic Amino Acid Decarboxylases Exhibit a pH Zone of Inhibition," *Biochemistry 50*, pp. 9388-9398 (2011).
Kanjee et al., "Linkage between the bacterial acid stress and stringent responses: the structure of the inducible lysine decarboxylase," *The EMBO Journal 30*, pp. 931-944 (2011).
Marc Lemonnier et al., "Expression of the second lysine decarboxylase gene of *Escherichia coli*," *Microbiology 144*, pp. 751-760 (1998).
Zhi-Gang Qian et al., "Metabolic Engineering of *Escherichia coli* for the Production of Cadaverine: A Five Carbon Diamine," *Biotechnology and Bioengineering*, vol. 108, No. 1, pp. 93-103 (2011).
Dongru Qiu, "PBAD-Based Shuttle Vectors for Functional Analysis of Toxic and Highly Regulated Genes in *Pseudomonas* and *Burkholderia* spp. and Other BacteriaV," *Applied and Environmental Microbiology*, vol. 74, No. 23, pp. 7422-7426 (2008).
Claire Vieille et al., "Hyperthermophilic Enzymes: Sources, Uses, and Molecular Mechanisms for Thermostability," *Microbiology and Molecular Biology Reviews*, vol. 65, No. 1, pp. 1-43 (2001).
Extended European Search Report for Application No. EP 17916605.3, dated Apr. 22, 2021.
Se Hyeon Park et al., "Cadaverine Production by Using Cross-Linked Enzyme Aggregate of *Escherichia coli* Lysine Decarboxylase," *J. Microbiol. Biotechnol.*, vol. 27, No. 2, pp. 289-296 (2017).
Supplementary Partial European Search Report for Application No. EP 17916605.3, dated Jan. 26, 2021.

(Continued)

*Primary Examiner* — David Steadman
(74) *Attorney, Agent, or Firm* — Marshall, Gerstein & Borun LLP

(57) ABSTRACT

The invention provides microorganisms genetically modified to overexpress thermophilic lysine decarboxylase polypeptides in a mesophilic host to enhance the production of lysine and lysine derivatives by the microorganism, method of generating such microorganism, and methods of producing lysine and lysine derivatives using the genetically modified microorganisms.

8 Claims, 2 Drawing Sheets
Specification includes a Sequence Listing.

(56) References Cited

OTHER PUBLICATIONS

Seongwook Jeong et al., "Alkaliphilic lysine decarboxylases for effective synthesis of cadaverine from L-lysine", Korean Journal of Chemical Engineering, vol. 33, No. 5, pp. 1530-1533 (2016).

Weichao Ma et al., "Advances in Cadaverine Bacterial Production and its Applications", Engineering, vol. 3, No. 3, pp. 308-317 (2017).

\* cited by examiner

```
LdcC         MNIIAIMGPHGVFYKDEPIKELESALVAQGFQIIWPQNSVDLLKFIEHNPRICGVIFDWD
CadA         MNVIAILNHMGVYFKEEPIRELHRALERLNFQIVYPNDRDDLLKLIENNARLCGVIFDWD
GAQ24853.1   ------------------------------------------------------------
BAC09418.1   ------------------------------------------------------------
BAD75350.1   ------------------------------------------------------------
ACM05730.1   ------------------------------------------------------------

LdcC         EYSLDLCSDINQLNEYLPLYAFINTHSTMDVSVQDMRMALWFFEYALGQAEDIAIRMRQY
CadA         KYNLELCEEISKMNENLPLYAFANTYSTLDVSLNDLRLQISFFEYALGAAEDIANKIKQT
GAQ24853.1   ----------------------------------------------------------ME
BAC09418.1   ------------------------------------------------------------
BAD75350.1   ------------------------------------------------------------
ACM05730.1   ------------------------------------------------------------

LdcC         TDEYLDNITPPFTKALFTYVKERKYTFCTPGHMGGTAYQKSPVGCLFYDFFGGNTLKADV
CadA         TDEYINTILPPLTKALFKYVREGKYTFCTPGHMGGTAFQKSPVGSLFYDFFGPNTMKSDI
GAQ24853.1   KQEINKFSKTPLIQALKEYEKKDSLRFHMPGHKGRCP--------KGVFCDIKENLFGWDV
BAC09418.1   ---------------------------M-----EPLLRALWG-TALEQDL
BAD75350.1   ----MSQLETPLFTGLLEHMKKNPVQFHIPGHKKGAGM------DPEFRAFIGDNALAIDL
ACM05730.1   --MSEEQQRAPYLEQWLAYVDECVIPFTTPGHKQGRGA------PPEFVAAFGERALALDI

LdcC         SISVTELGSLLDHTGPHLEAEEYIARTFGAEQSYIVTNGTSTSNKIVGMYAAPSGSTLLI
CadA         SISVSELGSLLDHSGPHKEAEQYIARVFNADRSYMVTNGTSTANKIVGMYSAPAGSTILI
GAQ24853.1   T-EIPGLDDFAQPEGPIKEAQEKLSALYGADTSYFLVNGATSGIISMMAGALSEKDKILI
BAC09418.1   S-ELPGLDNLAQPTGVLAEAQAVVAATVGSDRAWFLVNGATGGLLAALLATVGPGDRVLV
BAD75350.1   I-NISPLDDLHHPKGMIKRAQELAAEAFGADYTFFSVQGTSGAIMTMVMSVAGPGDKIIV
ACM05730.1   P-HDGGTFDAHLEHDPLVAAERLAAALWGARDAVFLVNGSTTGNLAALLTLGRPGQPIVV
                                             .   .     .           . :::

LdcC         DRNCHKSLAHLLMMNDVVPVWLKPTRN-ALGILGGIPRREFTRDSIEEKVAATTQAQWPV
CadA         DRNCHKSLTHLMMMSDVTPIYFRPTRN-AYGILGGIPQSEFQHATIAKRVKETPNATWPV
GAQ24853.1   PRTSHKSVLSGLILTGASAAYIMPERCEELGVYAQVEPCA------ITNKLIENPDIK---
BAC09418.1   GRNVHRSVIAGLVLAGAKPVYLGVGVDPQWGLPWPVTRDV------VAAGLAAYPDTK---
BAD75350.1   PRNVHKSVMSAIVFSGATPIFIHPEIDKELGISHGITPQA------VEKALRQHPDAK---
ACM05730.1   TRAMHKSLLAGLVLSGARPVYVVPAVHPESGILLDLPPES------VAQALAAWPDAT---
               * *:*:    :::  ..    :.      *:   :          :   :      :

LdcC         HAVITNSTYDGLLYNTDWIKQTLDV--PSIHFDSAWVPYTHFHPIYQGKSGMSGERVAGK
CadA         HAVITNSTYDGLLYNTDFIKKTLDV--KSIHFDSAWVPYTNFSPIYEGKCGMSGGRVEGK
GAQ24853.1   AILVTNPVYQGFCPDIARVAEIAKERGTTLLADEAQGPHFGFSKKVPQSAGK-FADA---
BAC09418.1   AVVLVSPTYEGLCSPLLEIAQCVHNHGVPLIVDEAHGSHFAYHPAFPVTALAAGADV---
BAD75350.1   GVLVINPTYFGIAGDLKKIVDIAHSYNVPVLVDEAHGVHIHFHEDLPLSAMQAGADM---
ACM05730.1   AVALVSPTYTGVTSDTAELAALCHAGVPLFVDEAWGPHLPFHPALPAAAIPSGADL---
              : . .* *.         :  .   :   : *.*  :  :              .

LdcC         VIFETQSTHKMLAALSQASLIHIKGEY-DEEAFNEAFMMHTTTSPSYPIVASVETAAAML
CadA         VIYETQSTHKLLAAFSQASMIHVKGDV-NEETFNEAYMMHTTTSPHYGIVASTETAAAMM
GAQ24853.1   ---WVQSPHKMLTSLTQSAWLHIKGNRIDKERLEDFLHIVTTSSPSYILMASLDGTRELI
BAC09418.1   ---VVQSWHKTLGTLTQTAVLHLKGERVSAERLSQALNLVQTSSPNYWLLAALEGAGVQM
BAD75350.1   ---AATSVHKLGGSLTQSSILNVREGLVSAKHVQAILSMLTTTSTSYLLLASLDVARKQL
ACM05730.1   ----AVTSLHKLAGSLTQTALLLMAGNLVDQAQLRAATAMVQTTSPAAFLYASLDAARRRL
               . * **    :::*::  :  .         :   :       *  : *:  : . :
```

FIG. 1A

```
LdcC         RGNPGKRLINRSVERALHFRKEVQRLREESDGWFFDIWQPPQVDEAECWPVAPGEQWHGF
CadA         KGNAGKRLINGSIERAIKFRKEIKRLRTESDGWFFDVWQPDHIDTTECWPLRSDSTWHGF
GAQ24853.1   E-ENGNSYIEKAVELAQKARYEINNSTVFYAPGQEILGKYGIS-----------------
BAC09418.1   A-QQGEQIYGRLLQWV---KTFEWPLPR---------WQPPGI-----------------
BAD75350.1   A-TKGRELIDKAIRLADWTRRQINEIPYLYCVGEEILGTEATY-----------------
ACM05730.1   A-LEGEQLLARTLELAEHARRELAAIPGLEVVGPEIVAGRPGA-----------------
                   *.         :. .   :

LdcC         NDADADHMFLDPVKVTILTPGMDEQGNMSEEGIPAALVAKFLD-ERGIVVEKTGPYNLLF
CadA         KNIDNEHMYLDPIKVTLLTPGMEKDGTMSDFGIPASIVAKYLD-EHGIVVEKTGPYNLLF
GAQ24853.1   ---------SQDPLHLMVNV----------SCAGYTGYDIEKALREDFSIYAEYADLCNVYF
BAC09418.1   ---------PQDPLRLTLGT----------WPIGLTGFALDELLQPQI--IAEFPSGRSLTF
BAD75350.1   ---------DYDPTKLIISV----------KELGLTGHDVERWLRETYNIEVELSDLYNILC
ACM05730.1   ---------GFDRTRLVVDV----------QGFGLTGLEVKRILRRDFRIAAEMADLVSVVF
                      *   ::  .          *    .  :  .*       .*    . .:

LdcC         LFSIGIDKTKAMGLLRGLTEFKRSYDLNLRIKNMLPDLYAEDPDFYRNMRIQDLAQGIHK
CadA         LFSIGIDKTKALSLLRALTDFKRAFDLNLRVKNMLPSLYREDPEFYENMRIQELAQNIHK
GAQ24853.1   LITFSNTLEDIKGLLAVLSHF-------KPLK--------------------------N
BAC09418.1   CLGLGTTQTMLETLADRLKSVYTEYCHNAPLPP-------------------------
BAD75350.1   IITPGDTEREASLLVEALRRLSKQFSHQAE-KGIK------------------------
ACM05730.1   LITIGDTPETIAALVAAFRALAADRTRPDCAAGRRA--------------------VRA
                :   .      *     :    .

LdcC         LIRKHDLPGLMLRAFDTLPEMIMTPHQAWQRQIKGEVETIALEQLVGRVSANMILPYPPG
CadA         LIVHHNLPDLMYRAFEVLPTMVMTPYAAFQKELHGMTEEVYLDEMVGRINANMILPYPPG
GAQ24853.1   KVK---------PCFWIKDLPKVALEPKKAFK-----LPAKSVPFKDSAGSVSKRPLVPYPPG
BAC09418.1   L----------AIPSIPSCQEPALSPREAYF----CPQRSIPLRAALNEISAETIAPYPPG
BAD75350.1   ----------PKVLLPDIPALALTPRDAFY----AETEVVPFHESAGRIIAEFVMVYPPG
ACM05730.1   LLR--------STGPIVAGAPQAMTPREAFF----APAERVPLADAVGRVAAEPVTPYPPG
                :          : * *:         . :      . : . :  ****

LdcC         VPLLMPGEMLTKESRTVLDFLLMLCSVGQHYPGFETDIHGAKQDEDGVYRVRVLKMAG*-
CadA         VPLVMPGEMITEESRPVLEFLQMLCEIGAHYPGFETDIHGAYRQADGRYTVKVLKEESK-
GAQ24853.1   APLVMPGEIIEKEH----IEMINEILNSGGYCQGVTSEKFI-----------QVVTDF---
BAC09418.1   IPTVIAGERFTESV---IATLQTLQELGAEMVGASDPTLQT----------LRICKV----
BAD75350.1   IPIFIPGEIITEEN---LKYIETNLAAGLPVQGPEDDTLQT----------LRVIKEYKPI
ACM05730.1   IPVLAPGEVVRPEV---VEFLQAGRAAGMRFNGASDPTLAT----------LRVVRA-----
             * . **  .   :         *    *                            ::

LdcC         -
CadA         -
GAQ24853.1   -
BAC09418.1   -
BAD75350.1   R
ACM05730.1   -
```

FIG. 1B

SEQUENCE LISTING

<160> NUMBER OF SEQ ID NOS: 29

<210> SEQ ID NO 1
<211> LENGTH: 482
<212> TYPE: PRT
<213> ORGANISM: Tepidanaerobacter syntrophicus

<400> SEQUENCE: 1

```
Met Glu Lys Gln Glu Ile Asn Lys Phe Ser Lys Thr Pro Leu Ile Gln
1               5                   10                  15

Ala Leu Lys Glu Tyr Glu Lys Lys Asp Ser Leu Arg Phe His Met Pro
            20                  25                  30

Gly His Lys Gly Arg Cys Pro Lys Gly Val Phe Cys Asp Ile Lys Glu
        35                  40                  45

Asn Leu Phe Gly Trp Asp Val Thr Glu Ile Pro Gly Leu Asp Asp Phe
    50                  55                  60

Ala Gln Pro Glu Gly Pro Ile Lys Glu Ala Gln Glu Lys Leu Ser Ala
65                  70                  75                  80

Leu Tyr Gly Ala Asp Thr Ser Tyr Phe Leu Val Asn Gly Ala Thr Ser
                85                  90                  95

Gly Ile Ile Ser Met Met Ala Gly Ala Leu Ser Glu Lys Asp Lys Ile
            100                 105                 110

Leu Ile Pro Arg Thr Ser His Lys Ser Val Leu Ser Gly Leu Ile Leu
        115                 120                 125

Thr Gly Ala Ser Ala Ala Tyr Ile Met Pro Glu Arg Cys Glu Glu Leu
    130                 135                 140

Gly Val Tyr Ala Gln Val Glu Pro Cys Ala Ile Thr Asn Lys Leu Ile
145                 150                 155                 160

Glu Asn Pro Asp Ile Lys Ala Ile Leu Val Thr Asn Pro Val Tyr Gln
                165                 170                 175

Gly Phe Cys Pro Asp Ile Ala Arg Val Ala Glu Ile Ala Lys Glu Arg
            180                 185                 190

Gly Thr Thr Leu Leu Ala Asp Glu Ala Gln Gly Pro His Phe Gly Phe
        195                 200                 205

Ser Lys Lys Val Pro Gln Ser Ala Gly Lys Phe Ala Asp Ala Trp Val
    210                 215                 220
```

```
Gln Ser Pro His Lys Met Leu Thr Ser Leu Thr Gln Ser Ala Trp Leu
225                 230                 235                 240

His Ile Lys Gly Asn Arg Ile Asp Lys Glu Arg Leu Glu Asp Phe Leu
            245                 250                 255

His Ile Val Thr Thr Ser Ser Pro Ser Tyr Ile Leu Met Ala Ser Leu
        260                 265                 270

Asp Gly Thr Arg Glu Leu Ile Glu Glu Asn Gly Asn Ser Tyr Ile Glu
        275                 280                 285

Lys Ala Val Glu Leu Ala Gln Lys Ala Arg Tyr Glu Ile Asn Asn Ser
290                 295                 300

Thr Val Phe Tyr Ala Pro Gly Gln Glu Ile Leu Gly Lys Tyr Gly Ile
305                 310                 315                 320

Ser Ser Gln Asp Pro Leu His Leu Met Val Asn Val Ser Cys Ala Gly
                325                 330                 335

Tyr Thr Gly Tyr Asp Ile Glu Lys Ala Leu Arg Glu Asp Phe Ser Ile
            340                 345                 350

Tyr Ala Glu Tyr Ala Asp Leu Cys Asn Val Tyr Phe Leu Ile Thr Phe
        355                 360                 365

Ser Asn Thr Leu Glu Asp Ile Lys Gly Leu Leu Ala Val Leu Ser His
    370                 375                 380

Phe Lys Pro Leu Lys Asn Lys Val Lys Pro Cys Phe Trp Ile Lys Asp
385                 390                 395                 400

Leu Pro Lys Val Ala Leu Glu Pro Lys Lys Ala Phe Lys Leu Pro Ala
                405                 410                 415

Lys Ser Val Pro Phe Lys Asp Ser Ala Gly Ser Val Ser Lys Arg Pro
            420                 425                 430

Leu Val Pro Tyr Pro Pro Gly Ala Pro Leu Val Met Pro Gly Glu Ile
        435                 440                 445

Ile Glu Lys Glu His Ile Glu Met Ile Asn Glu Ile Leu Asn Ser Gly
    450                 455                 460

Gly Tyr Cys Gln Gly Val Thr Ser Glu Lys Phe Ile Gln Val Val Thr
465                 470                 475                 480

Asp Phe

<210> SEQ ID NO 2
<211> LENGTH: 490
<212> TYPE: PRT
<213> ORGANISM: Geobacillus kaustophilus

<400> SEQUENCE: 2

Met Ser Gln Leu Glu Thr Pro Leu Phe Thr Gly Leu Leu Glu His Met
1               5                   10                  15

Lys Lys Asn Pro Val Gln Phe His Ile Pro Gly His Lys Lys Gly Ala
            20                  25                  30

Gly Met Asp Pro Glu Phe Arg Ala Phe Ile Gly Asp Asn Ala Leu Ala
        35                  40                  45

Ile Asp Leu Ile Asn Ile Ser Pro Leu Asp Asp His His Pro Lys
    50                  55                  60

Gly Met Ile Lys Arg Ala Gln Glu Leu Ala Glu Ala Phe Gly Ala
65                  70                  75                  80

Asp Tyr Thr Phe Phe Ser Val Gln Gly Thr Ser Gly Ala Ile Met Thr
            85                  90                  95

Met Val Met Ser Val Ala Gly Pro Gly Asp Lys Ile Ile Val Pro Arg
        100                 105                 110
```

-continued

Asn Val His Lys Ser Val Met Ser Ala Ile Val Phe Ser Gly Ala Thr
            115                 120                 125

Pro Ile Phe Ile His Pro Glu Ile Asp Lys Glu Leu Gly Ile Ser His
130                 135                 140

Gly Ile Thr Pro Gln Ala Val Glu Lys Ala Leu Arg Gln His Pro Asp
145                 150                 155                 160

Ala Lys Gly Val Leu Val Ile Asn Pro Thr Tyr Phe Gly Ile Ala Gly
                165                 170                 175

Asp Leu Lys Lys Ile Val Asp Ile Ala His Ser Tyr Asn Val Pro Val
            180                 185                 190

Leu Val Asp Glu Ala His Gly Val His Ile His Phe His Glu Asp Leu
        195                 200                 205

Pro Leu Ser Ala Met Gln Ala Gly Ala Asp Met Ala Ala Thr Ser Val
210                 215                 220

His Lys Leu Gly Gly Ser Leu Thr Gln Ser Ser Ile Leu Asn Val Arg
225                 230                 235                 240

Glu Gly Leu Val Ser Ala Lys His Val Gln Ala Ile Leu Ser Met Leu
                245                 250                 255

Thr Thr Thr Ser Thr Ser Tyr Leu Leu Leu Ala Ser Leu Asp Val Ala
            260                 265                 270

Arg Lys Gln Leu Ala Thr Lys Gly Arg Glu Leu Ile Asp Lys Ala Ile
        275                 280                 285

Arg Leu Ala Asp Trp Thr Arg Arg Gln Ile Asn Glu Ile Pro Tyr Leu
    290                 295                 300

Tyr Cys Val Gly Glu Glu Ile Leu Gly Thr Glu Ala Thr Tyr Asp Tyr
305                 310                 315                 320

Asp Pro Thr Lys Leu Ile Ile Ser Val Lys Glu Leu Gly Leu Thr Gly
                325                 330                 335

His Asp Val Glu Arg Trp Leu Arg Glu Thr Tyr Asn Ile Glu Val Glu
            340                 345                 350

Leu Ser Asp Leu Tyr Asn Ile Leu Cys Ile Ile Thr Pro Gly Asp Thr
        355                 360                 365

Glu Arg Glu Ala Ser Leu Leu Val Glu Ala Leu Arg Arg Leu Ser Lys
    370                 375                 380

Gln Phe Ser His Gln Ala Glu Lys Gly Ile Lys Pro Lys Val Leu Leu
385                 390                 395                 400

Pro Asp Ile Pro Ala Leu Ala Leu Thr Pro Arg Asp Ala Phe Tyr Ala
                405                 410                 415

Glu Thr Glu Val Val Pro Phe His Glu Ser Ala Gly Arg Ile Ile Ala
            420                 425                 430

Glu Phe Val Met Val Tyr Pro Pro Gly Ile Pro Ile Phe Ile Pro Gly
        435                 440                 445

Glu Ile Ile Thr Glu Glu Asn Leu Lys Tyr Ile Glu Thr Asn Leu Ala
    450                 455                 460

Ala Gly Leu Pro Val Gln Gly Pro Glu Asp Asp Thr Leu Gln Thr Leu
465                 470                 475                 480

Arg Val Ile Lys Glu Tyr Lys Pro Ile Arg
                485                 490

<210> SEQ ID NO 3
<211> LENGTH: 437
<212> TYPE: PRT
<213> ORGANISM: Thermosynechoccus elongatus

<400> SEQUENCE: 3

-continued

```
Met Glu Pro Leu Leu Arg Ala Leu Trp Gly Thr Ala Leu Glu Gln Asp
 1               5                  10                  15

Leu Ser Glu Leu Pro Gly Leu Asp Asn Leu Ala Gln Pro Thr Gly Val
            20                  25                  30

Leu Ala Glu Ala Gln Ala Val Val Ala Thr Val Gly Ser Asp Arg
        35                  40                  45

Ala Trp Phe Leu Val Asn Gly Ala Thr Gly Gly Leu Leu Ala Ala Leu
 50                  55                  60

Leu Ala Thr Val Gly Pro Gly Asp Arg Val Leu Val Gly Arg Asn Val
 65              70                  75                  80

His Arg Ser Val Ile Ala Gly Leu Val Leu Ala Gly Ala Lys Pro Val
                 85                  90                  95

Tyr Leu Gly Val Gly Val Asp Pro Gln Trp Gly Leu Pro Trp Pro Val
                100                 105                 110

Thr Arg Asp Val Val Ala Ala Gly Leu Ala Ala Tyr Pro Asp Thr Lys
            115                 120                 125

Ala Val Val Leu Val Ser Pro Thr Tyr Glu Gly Leu Cys Ser Pro Leu
        130                 135                 140

Leu Glu Ile Ala Gln Cys Val His Asn His Gly Val Pro Leu Ile Val
145                 150                 155                 160

Asp Glu Ala His Gly Ser His Phe Ala Tyr His Pro Ala Phe Pro Val
                165                 170                 175

Thr Ala Leu Ala Ala Gly Ala Asp Val Val Gln Ser Trp His Lys
            180                 185                 190

Thr Leu Gly Thr Leu Thr Gln Thr Ala Val Leu His Leu Lys Gly Glu
        195                 200                 205

Arg Val Ser Ala Glu Arg Leu Ser Gln Ala Leu Asn Leu Val Gln Thr
210                 215                 220

Ser Ser Pro Asn Tyr Trp Leu Leu Ala Leu Glu Gly Ala Gly Val
225                 230                 235                 240

Gln Met Ala Gln Gln Gly Glu Gln Ile Tyr Gly Arg Leu Leu Gln Trp
                245                 250                 255

Val Lys Thr Phe Glu Trp Pro Leu Pro Arg Trp Gln Pro Gly Ile
            260                 265                 270

Pro Gln Asp Pro Leu Arg Leu Thr Leu Gly Thr Trp Pro Ile Gly Leu
        275                 280                 285

Thr Gly Phe Ala Leu Asp Glu Leu Leu Gln Pro Gln Ile Ile Ala Glu
    290                 295                 300

Phe Pro Ser Gly Arg Ser Leu Thr Phe Cys Leu Gly Leu Gly Thr Thr
305                 310                 315                 320

Gln Thr Met Leu Glu Thr Leu Ala Asp Arg Leu Lys Ser Val Tyr Thr
                325                 330                 335

Glu Tyr Cys His Asn Ala Pro Leu Pro Pro Leu Ala Ile Pro Ser Ile
            340                 345                 350

Pro Ser Cys Gln Glu Pro Ala Leu Ser Pro Arg Glu Ala Tyr Phe Cys
        355                 360                 365

Pro Gln Arg Ser Ile Pro Leu Arg Ala Ala Leu Asn Glu Ile Ser Ala
    370                 375                 380

Glu Thr Ile Ala Pro Tyr Pro Pro Gly Ile Pro Thr Val Ile Ala Gly
385                 390                 395                 400

Glu Arg Phe Thr Glu Ser Val Ile Ala Thr Leu Gln Thr Leu Gln Glu
                405                 410                 415
```

Leu Gly Ala Glu Met Val Gly Ala Ser Asp Pro Thr Leu Gln Thr Leu
            420                 425                 430
Arg Ile Cys Lys Val
            435

<210> SEQ ID NO 4
<211> LENGTH: 495
<212> TYPE: PRT
<213> ORGANISM: Thermomicrobium roseum

<400> SEQUENCE: 4

Met Ser Glu Glu Gln Gln Arg Ala Pro Tyr Leu Glu Gln Trp Leu Ala
1               5                   10                  15

Tyr Val Asp Glu Cys Val Ile Pro Phe Thr Thr Pro Gly His Lys Gln
            20                  25                  30

Gly Arg Gly Ala Pro Pro Glu Phe Val Ala Ala Phe Gly Glu Arg Ala
        35                  40                  45

Leu Ala Leu Asp Ile Pro His Asp Gly Gly Thr Phe Asp Ala His Leu
    50                  55                  60

Glu His Asp Pro Leu Val Ala Ala Glu Arg Leu Ala Ala Ala Leu Trp
65                  70                  75                  80

Gly Ala Arg Asp Ala Val Phe Leu Val Asn Gly Ser Thr Thr Gly Asn
                85                  90                  95

Leu Ala Ala Leu Leu Thr Leu Gly Arg Pro Gly Gln Pro Ile Val Val
            100                 105                 110

Thr Arg Ala Met His Lys Ser Leu Leu Ala Gly Leu Val Leu Ser Gly
        115                 120                 125

Ala Arg Pro Val Tyr Val Val Pro Ala Val His Pro Glu Ser Gly Ile
    130                 135                 140

Leu Leu Asp Leu Pro Pro Glu Ser Val Ala Gln Ala Leu Ala Ala Trp
145                 150                 155                 160

Pro Asp Ala Thr Ala Val Ala Leu Val Ser Pro Thr Tyr Thr Gly Val
                165                 170                 175

Thr Ser Asp Thr Ala Glu Leu Ala Ala Leu Cys His Ala His Gly Val
            180                 185                 190

Pro Leu Phe Val Asp Glu Ala Trp Gly Pro His Leu Pro Phe His Pro
        195                 200                 205

Ala Leu Pro Ala Ala Ala Ile Pro Ser Gly Ala Asp Leu Ala Val Thr
    210                 215                 220

Ser Leu His Lys Leu Ala Gly Ser Leu Thr Gln Thr Ala Leu Leu Leu
225                 230                 235                 240

Met Ala Gly Asn Leu Val Asp Gln Ala Gln Leu Arg Ala Ala Thr Ala
                245                 250                 255

Met Val Gln Thr Thr Ser Pro Ala Ala Phe Leu Tyr Ala Ser Leu Asp
            260                 265                 270

Ala Ala Arg Arg Arg Leu Ala Leu Glu Gly Glu Gln Leu Leu Ala Arg
        275                 280                 285

Thr Leu Glu Leu Ala Glu His Ala Arg Arg Glu Leu Ala Ala Ile Pro
    290                 295                 300

Gly Leu Glu Val Val Gly Pro Glu Ile Val Ala Gly Arg Pro Gly Ala
305                 310                 315                 320

Gly Phe Asp Arg Thr Arg Leu Val Val Asp Val Gln Gly Phe Gly Leu
                325                 330                 335

Thr Gly Leu Glu Val Lys Arg Ile Leu Arg Arg Asp Phe Arg Ile Ala
            340                 345                 350

```
Ala Glu Met Ala Asp Leu Val Ser Val Val Phe Leu Ile Thr Ile Gly
            355                 360                 365

Asp Thr Pro Glu Thr Ile Ala Ala Leu Val Ala Ala Phe Arg Ala Leu
    370                 375                 380

Ala Ala Asp Arg Thr Arg Pro Asp Cys Ala Ala Gly Arg Arg Ala Val
385                 390                 395                 400

Arg Ala Leu Leu Arg Ser Thr Gly Pro Ile Val Ala Gly Ala Pro Gln
                405                 410                 415

Ala Met Thr Pro Arg Glu Ala Phe Phe Ala Pro Ala Glu Arg Val Pro
            420                 425                 430

Leu Ala Asp Ala Val Gly Arg Val Ala Ala Glu Pro Val Thr Pro Tyr
        435                 440                 445

Pro Pro Gly Ile Pro Val Leu Ala Pro Gly Val Val Arg Pro Glu
    450                 455                 460

Val Val Glu Phe Leu Gln Ala Gly Arg Ala Ala Gly Met Arg Phe Asn
465                 470                 475                 480

Gly Ala Ser Asp Pro Thr Leu Ala Thr Leu Arg Val Val Arg Ala
                485                 490                 495

<210> SEQ ID NO 5
<211> LENGTH: 1449
<212> TYPE: DNA
<213> ORGANISM: Tepidanaerobacter syntrophicus

<400> SEQUENCE: 5
atggagaagc aagagattaa caagttctct aagaccccgc tcatccaagc gctgaaagaa      60
tacgagaaaa aggattctct gcgtttccac atgccaggtc acaaggccg ttgtccaaaa      120 ggtgtttttt gcgatattaa ggagaacctg ttcggttggg atgttaccga atcccgggt      180 ctggatgact cgctcaacc ggaaggtccg atcaaggaag cacaggagaa actgtctgcg      240
ctgtacggtg ccgacacctc ctatttcctc gttaatggtg caacctctgg tatcatttct      300
atgatggcgg gtgctctgtc cgaaaaggac aaaatcctga tcccgcgtac cagccataag      360
agcgtactct ctggtctgat tctcactggc gcctctgcgg cgtacatcat gccggagcgt      420
tgcgaagagc tgggtgttta cgcacaggtg gaaccttgtg ccatcaccaa caaactgatc      480
gagaacccgg atatcaaagc gattctggtt accaacccag tgtaccaggg ttctgcccg      540 gacatcgcgc gtgttgcgga atcgcgaaaa gaacgcggta ccaccctgct cgcagacgaa      600
gcgcaaggcc acatttcgg cttttccaag aaagttccgc agtctgcggg taagttcgcg      660
gatgcgtggg ttcagtcccc tcacaaaatg ctgacgagcc tgacccaatc tgcgtggctg      720
cacatcaagg gcaatcgtat cgacaaggaa cgtctggaag actttctcca tcgttacc      780 acctcttctc gtcttacat cctcatggcg tctctggacg gtacccgcga gctgattgaa      840
gaaaacggta actcctacat tgaaaaggcg gttgaactgg ctcagaaagc gcgttatgaa      900
atcaacaact ctactgtttt ctacgcgcca ggccaggaga ttctcggtaa atacggtatt      960
tcttctcagg acccgctgca tctgatggtt aatgtttctt gcgcgggtta cacgggctac     1020
gacatcgaaa aagccctgcg tgaggacttt tctatctacg ccgaatacgc ggacctgtgt     1080
aacgtttact tcctcattac gtttagcaat accctggagg acattaaagg tctcctcgcg     1140
gttctgtctc acttcaaacc gctcaaaaac aaagttaaac cgtgcttctg gatcaaagac     1200
ctgccgaaag ttgcgctgga gccaagaag gcgttcaaac tgccggcgaa atctgtgcct     1260
ttcaaagatt ctgctggtag cgtttctaaa cgcccgctgg ttccgtatcc gccaggtgcg     1320
```

```
ccactcgtga tgccgggtga gatcattgag aaagagcaca tcgagatgat taatgaaatt    1380
ctcaactctg gcggctactg ccagggtgtt acgtctgaaa agttcattca ggttgtaacc    1440
gatttctaa                                                             1449
```

<210> SEQ ID NO 6
<211> LENGTH: 1473
<212> TYPE: DNA
<213> ORGANISM: Geobacillus kaustophilus

<400> SEQUENCE: 6

```
atgtctcagc tcgagacccc tctgttcacc ggtctgctcg aacacatgaa gaaaaacccg     60
gtccagtttc acattccagg tcacaagaaa ggtgctggta tggaccctga gttccgtgcg    120
tttatcggtg ataacgcgct cgcgatcgac ctgatcaaca tctcccctct cgacgacctc    180
caccacccga aaggcatgat caaacgtgcg caggaactgg ctgcggaagc gtttggcgcg    240
gactacacgt tcttcagcgt tcaaggcacc agcggtgcca tcatgacgat ggtaatgtct    300
gttgcgggtc cggcgataaa gatcatcgtc cctcgtaacg ttcacaaatc tgttatgtct    360
gccatcgttt tctctggcgc gacccctatt ttcatccacc cggaaatcga taaggagctg    420
ggtattagcc acggtattac cccgcaggcc gtggagaaag ccctgcgtca caccctgat     480 gctaaaggcg ttctggtaat caacccgact tatttcggta tcgcgggtga cctcaaaaag    540
atcgttgaca tcgcgcactc ttataatgtg ccggtcctgg tagatgaagc gcacggtgtt    600
catattcact ccacgagga cctcccactc agcgcaatgc aggcgggtgc ggatatggcg    660
gcgacgtccg tgcacaagct gggcggtagc ctgactcagt cttccattct gaacgtacgc    720
gaaggtctgg tttctgctaa acacgtgcaa gcgattctct ctatgctgac caccacttct    780
acctcttatc tgctgctggc ttccctggac gtagcgcgta acagctggc aaccaaaggt    840 cgtgaactca tcgacaaagc catccgcctc gcggattgga cccgtcgcca gattaacgag    900
atcccgtacc tctactgcgt gggtgaagag atcctgggta ccgaagcaac ctacgactac    960
gatccgacta aactgatcat cagcgtaaaa gaactcggtc tcactggcca tgacgttgag    1020
cgttggctcc gtgaaaccta caatatcgaa gttgaactgt ctgacctcta acatcctc    1080 tgcatcatca cccggggtga tactgagcgc gaagcgtctc tcctggtgga agcactgcgc    1140
cgtctgtcta acaattctc ccatcaggcc gaaaagggta tcaaacctaa ggttctcctg    1200
ccggatattc ctgccctcgc cctgacgcct cgtgacgcgt tctatgcgga aaccgaagtc    1260
gttccgttcc atgagtccgc cggtcgtatc atcgcggagt ttgtaatggt ttacccaccg    1320
ggcatcccaa tcttcatccc tggcgagatt atcactgagg aaaacctgaa atacatcgaa    1380
accaacctgg cggctggcct cccggttcag ggcccagaag acgacacgct gcagaccctc    1440
cgtgtcatta agaatacaa accaattcgt taa                                  1473
```

<210> SEQ ID NO 7
<211> LENGTH: 1314
<212> TYPE: DNA
<213> ORGANISM: Thermosynechoccus elongatus

<400> SEQUENCE: 7

```
atggaacctc tgctgcgtgc gctgtgggt actgcactcg aacaagacct gtctgagctg      60
ccgggtctcg ataacctggc gcaaccgacc ggtgttctcg cagaagcgca ggctgttgtt    120
gcggcaactg taggttctga ccgtgcgtgg tttctggtta atggtgcaac gggcggtctc    180
```

```
ctcgccgcac tcctggccac cgtaggtcct ggtgatcgtg tgctggttgg ccgtaatgtt      240
caccgttctg ttatcgcagg tctcgttctg gcaggtgcaa agccggttta cctgggtgtt      300
ggtgtagatc cgcaatgggg tctgccgtgg ccggtaactc gtgatgtggt agccgctggt      360
ctggccgcat atccggacac caaagcggtt gtgctcgttt ctccgacgta tgaaggcctg      420
tgcagcccac tgctggagat cgcgcaatgc gttcacaacc acggtgtccc gctgatcgtt      480
gacgaagcac atggttctca cttcgcgtat cacccagctt tcccggtgac ggcgctcgct      540
gctggcgctg acgttgtcgt acagtcttgg cataaaaccc tgggtacgct gacccagacg      600
gcggttctcc acctcaaagg tgagcgtgtt ccgccgaac gtctgtctca ggctctgaac       660
ctggttcaaa cctcttcccc gaactactgg ctgctcgcag cactggaagg tgcaggcgtc      720
caaatggctc agcagggtga gcagatttac ggtcgcctgc tccagtgggt aaagaccttc      780
gaatggccac tcccgcgttg gcagccgcct ggcatccctc aggaccctct ccgtctcact      840
ctgggcactt ggcctattgg tctgacgggt ttcgcgctcg acgaactcct ccagccgcag      900
atcatcgcgg agttcccgtc cggtcgttcc ctcacgtttt gcctcggtct cggtaccacc      960
caaaccatgc tcgaaacgct ggcggaccgc ctgaaatctg tttacaccga atactgccac     1020
aacgcccctc tgcctcctct cgcgattcca tctatcccgt cttgccagga acctgctctc     1080
agcccgcgtg aagcgtactt ctgcccgcag cgctctattc cgctccgcgc agctctcaac     1140
gaaatctctg cggagaccat cgcgccgtat ccaccgggta tcccgaccgt gatcgcgggt     1200
gaacgtttca cggaatctgt catcgcaacc ctccagaccc tgcaagaact cggtgcagaa     1260
atggtcggtg cgagcgaccc tacgctgcag actctgcgta tctgcaaagt ttaa           1314
```

<210> SEQ ID NO 8
<211> LENGTH: 1488
<212> TYPE: DNA
<213> ORGANISM: Thermomicrobium roseum

<400> SEQUENCE: 8

```
atgtctgaag aacagcaacg tgctccgtac ctggagcaat ggctggcgta cgttgacgag       60
tgcgttatcc cgtttaccac tccgggtcac aaacaaggtc gcggtgcgcc accggagttc      120
gttgcggcgt tcggtgaacg tgcgctcgct ctggacattc gcatgacgg tggcaccttt       180
gacgcgcatc tggaacatga cccgctcgtt gccgccgaac gtctggctgc cgcactgtgg      240
ggtgcacgcg atgcggtgtt tctggttaac ggttccacca ctggtaacct ggcggctctg      300
ctcactctcg gtcgcccagg tcagccgatt gttgttactc gtgccatgca taagagcctg      360
ctggcaggtc tggtcctgag cggtgctcgc cctgtctacg ttgtaccggc cgtacaccca      420
gaatccggta tcctcctcga tctccctccg gaatctgttg cgcaggcgct ggccgcgtgg      480
cctgatgcga cggctgtagc tctggtgtcc ccgacctaca ctggcgttac ctctgacact      540
gctgaactgg cagccctctg tcacgctcat ggtgttccac tgtttgttga tgaagcgtgg      600
ggtccgcacc tcccgttcca tccagcactc ccagcagcag ctattccgtc tggtgccgat      660
ctggcggtta cttctctgca caaactggcg ggttccctca cccaaaccgc tctcctcctg      720
atggcaggca acctcgtaga ccaagcccag ctgcgtgcag ccacggcaat ggtgcaaacc      780
accagccctg cagccttcct gtacgcgtcc ctggatgctg cccgtcgccg tctcgcgctc      840
gaaggtgaac agctcctcgc acgtactctc gagctggctg agcacgctcg ccgtgaactc      900
gccgccatcc cggtctgga ggtggtcggt ccagaaattg ttgcgggtcg tccgggtgcc       960
ggcttcgatc gtactcgcct cgttgttgac gttcagggtt tcggtctgac tggcctcgaa     1020
```

-continued

```
gtaaagcgta tcctgcgtcg tgacttccgt attgcagctg aaatggcaga tctcgtctct   1080
gttgttttcc tcatcaccat cggtgacacc ccagagacca tcgctgccct ggtagcagct   1140
ttccgtgcac tcgctgctga ccgtacccgt ccagactgtg ctgccggtcg tcgtgcagta   1200
cgcgccctcc tccgttctac cggtccgatc gtcgcgggtg ctcctcaggc gatgaccccg   1260
cgtgaagctt tcttcgctcc agctgagcgc gttccgctcg cggatgccgt cggtcgtgtt   1320
gcagccgagc cggttacccc atatccgcct ggtattccgg tactggcccc aggtgaagtg   1380
gttcgcccgg aggtagttga attcctccag gcaggccgtg ccgctggtat gcgtttcaat   1440
ggcgcgtctg acccgactct ggcgaccctc cgtgtcgttc gtgcctaa               1488
```

<210> SEQ ID NO 9
<211> LENGTH: 715
<212> TYPE: PRT
<213> ORGANISM: Escherichia coli

<400> SEQUENCE: 9

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285
```

```
Val Lys Glu Thr Pro Asn Ala Thr Trp Pro Val His Ala Val Ile Thr
290                 295                 300
Asn Ser Thr Tyr Asp Gly Leu Leu Tyr Asn Thr Asp Phe Ile Lys Lys
305                 310                 315                 320
Thr Leu Asp Val Lys Ser Ile His Phe Asp Ser Ala Trp Val Pro Tyr
                325                 330                 335
Thr Asn Phe Ser Pro Ile Tyr Glu Gly Lys Cys Gly Met Ser Gly Gly
                340                 345                 350
Arg Val Glu Gly Lys Val Ile Tyr Glu Thr Gln Ser Thr His Lys Leu
                355                 360                 365
Leu Ala Ala Phe Ser Gln Ala Ser Met Ile His Val Lys Gly Asp Val
370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
                405                 410                 415
Lys Gly Asn Ala Gly Lys Arg Leu Ile Asn Gly Ser Ile Glu Arg Ala
                420                 425                 430
Ile Lys Phe Arg Lys Glu Ile Lys Arg Leu Arg Thr Glu Ser Asp Gly
                435                 440                 445
Trp Phe Phe Asp Val Trp Gln Pro Asp His Ile Asp Thr Thr Glu Cys
450                 455                 460
Trp Pro Leu Arg Ser Asp Ser Thr Trp His Gly Phe Lys Asn Ile Asp
465                 470                 475                 480
Asn Glu His Met Tyr Leu Asp Pro Ile Lys Val Thr Leu Leu Thr Pro
                485                 490                 495
Gly Met Glu Lys Asp Gly Thr Met Ser Asp Phe Gly Ile Pro Ala Ser
                500                 505                 510
Ile Val Ala Lys Tyr Leu Asp Glu His Gly Ile Val Val Glu Lys Thr
                515                 520                 525
Gly Pro Tyr Asn Leu Leu Phe Leu Phe Ser Ile Gly Ile Asp Lys Thr
530                 535                 540
Lys Ala Leu Ser Leu Leu Arg Ala Leu Thr Asp Phe Lys Arg Ala Phe
545                 550                 555                 560
Asp Leu Asn Leu Arg Val Lys Asn Met Leu Pro Ser Leu Tyr Arg Glu
                565                 570                 575
Asp Pro Glu Phe Tyr Glu Asn Met Arg Ile Gln Glu Leu Ala Gln Asn
                580                 585                 590
Ile His Lys Leu Ile Val His His Asn Leu Pro Asp Leu Met Tyr Arg
                595                 600                 605
Ala Phe Glu Val Leu Pro Thr Met Val Met Thr Pro Tyr Ala Ala Phe
610                 615                 620
Gln Lys Glu Leu His Gly Met Thr Glu Glu Val Tyr Leu Asp Glu Met
625                 630                 635                 640
Val Gly Arg Ile Asn Ala Asn Met Ile Leu Pro Tyr Pro Pro Gly Val
                645                 650                 655
Pro Leu Val Met Pro Gly Glu Met Ile Thr Glu Glu Ser Arg Pro Val
                660                 665                 670
Leu Glu Phe Leu Gln Met Leu Cys Glu Ile Gly Ala His Tyr Pro Gly
                675                 680                 685
Phe Glu Thr Asp Ile His Gly Ala Tyr Arg Gln Ala Asp Gly Arg Tyr
690                 695                 700
Thr Val Lys Val Leu Lys Glu Glu Ser Lys Lys
```

<210> SEQ ID NO 10
<211> LENGTH: 2148
<212> TYPE: DNA
<213> ORGANISM: Escherichia coli

<400> SEQUENCE: 10

| | | | | | | |
|---|---|---|---|---|---|---|
| atgaacgtta | ttgcaatatt | gaatcacatg | ggggtttatt | ttaaagaaga | acccatccgt | 60 |
| gaacttcatc | gcgcgcttga | acgtctgaac | ttccagattg | tttacccgaa | cgaccgtgac | 120 |
| gacttattaa | aactgatcga | aaacaatgcg | cgtctgtgcg | gcgttatttt | tgactgggat | 180 |
| aaatataatc | tcgagctgtg | cgaagaaatt | agcaaaatga | acgagaacct | gccgttgtac | 240 |
| gcgttcgcta | atacgtattc | cactctcgat | gtaagcctga | atgacctgcg | tttacagatt | 300 |
| agcttctttg | aatatgcgct | gggtgctgct | gaagatattg | ctaataagat | caagcagacc | 360 |
| actgacgaat | atatcaacac | tattctgcct | ccgctgacta | agcactgtt | taaatatgtt | 420 |
| cgtgaaggta | aatatacttt | ctgtactcct | ggtcacatgg | gcggtactgc | attccagaaa | 480 |
| agcccggtag | gtagcctgtt | ctatgatttc | tttggtccga | ataccatgaa | atctgatatt | 540 |
| tccatttcag | tatctgaact | gggttctctg | ctggatcaca | gtggtccaca | caaagaagca | 600 |
| gaacagtata | tcgctcgcgt | ctttaacgca | gaccgcagct | acatggtgac | caacggtact | 660 |
| tccactgcga | acaaaattgt | tggtatgtac | tctgctccag | caggcagcac | cattctgatt | 720 |
| gaccgtaact | gccacaaatc | gctgacccac | ctgatgatga | tgagcgatgt | tacgccaatc | 780 |
| tatttccgcc | cgaccgtaa | cgcttacggt | attcttggtg | gtatcccaca | gagtgaattc | 840 |
| cagcacgcta | ccattgctaa | gcgcgtgaaa | gaaacaccaa | acgcaacctg | gccggtacat | 900 |
| gctgtaatta | ccaactctac | ctatgatggt | ctgctgtaca | acaccgactt | catcaagaaa | 960 |
| acactggatg | tgaaatccat | ccactttgac | tccgcgtggg | tgccttacac | caacttctca | 1020 |
| ccgatttacg | aaggtaaatg | cggtatgagc | ggtggccgtg | tagaagggaa | agtgatttac | 1080 |
| gaaacccagt | ccactcacaa | actgctggcg | gcgttctctc | aggcttccat | gatccacgtt | 1140 |
| aaaggtgacg | taaacgaaga | aaccttaaac | gaagcctaca | tgatgcacac | caccacttct | 1200 |
| ccgcactacg | gtatcgtggc | gtccactgaa | accgctgcgg | cgatgatgaa | aggcaatgca | 1260 |
| ggtaagcgtc | tgatcaacgg | ttctattgaa | cgtgcgatca | aattccgtaa | agagatcaaa | 1320 |
| cgtctgagaa | cggaatctga | tggctggttc | tttgatgtat | ggcagccgga | tcatatcgat | 1380 |
| acgactgaat | gctggcccgct | gcgttctgac | agcacctggc | acggcttcaa | aaacatcgat | 1440 |
| aacgagcaca | tgtatcttga | cccgatcaaa | gtcaccctgc | tgactccggg | gatggaaaaa | 1500 |
| gacggcacca | tgagcgactt | tggtattccg | ccagcatcg | tggcgaaata | cctcgacgaa | 1560 |
| catggcatcg | ttgttgagaa | aaccggtccg | tataacctgc | tgttcctgtt | cagcatcggt | 1620 |
| atcgataaga | ccaaagcact | gagcctgctg | cgtgctctga | ctgactttaa | acgtgcgttc | 1680 |
| gacctgaacc | tgcgtgtgaa | aaacatgctg | ccgtctctgt | atcgtgaaga | tcctgaattc | 1740 |
| tatgaaaaca | tgcgtattca | ggaactggct | cagaatatcc | acaaactgat | tgttcaccac | 1800 |
| aatctgccgg | atctgatgta | tcgcgcattt | gaagtgctgc | cgacgatggt | aatgactccg | 1860 |
| tatgctgcat | tccagaaaga | gctgcacggt | atgaccgaag | aagtttacct | cgacgaaatg | 1920 |
| gtaggtcgta | ttaacgccaa | tatgatcctt | ccgtacccgc | cgggagttcc | tctggtaatg | 1980 |
| ccgggtgaaa | tgatcaccga | agaaagccgt | ccggttctgg | agttcctgca | gatgctgtgt | 2040 |
| gaaatcggcg | ctcactatcc | gggctttgaa | accgatattc | acggtgcata | ccgtcaggct | 2100 | gatggccgct ataccgttaa ggtattgaaa gaagaaagca aaaaataa        2148

<210> SEQ ID NO 11
<211> LENGTH: 52
<212> TYPE: DNA
<213> ORGANISM: Artificial Sequence
<220> FEATURE:
<223> OTHER INFORMATION: Primer cadA-F

<400> SEQUENCE: 11
ggcgagctca cacaggaaac agaccatgaa cgttattgca atattgaatc ac        52

<210> SEQ ID NO 12
<211> LENGTH: 28
<212> TYPE: DNA
<213> ORGANISM: Artificial Sequence
<220> FEATURE:
<223> OTHER INFORMATION: Primer cadA-R

<400> SEQUENCE: 12
ggctctagac cacttcccctt gtacgagc        28

<210> SEQ ID NO 13
<211> LENGTH: 44
<212> TYPE: DNA
<213> ORGANISM: Artificial Sequence
<220> FEATURE:
<223> OTHER INFORMATION: Primer cadA-F2

<400> SEQUENCE: 13
atttcacaca ggaaacagct atgaacgtta ttgcaatatt gaat        44

<210> SEQ ID NO 14
<211> LENGTH: 20
<212> TYPE: DNA
<213> ORGANISM: Artificial Sequence
<220> FEATURE:
<223> OTHER INFORMATION: Primer cadA-R2

<400> SEQUENCE: 14
agctgtttcc tgtgtgaaat        20

<210> SEQ ID NO 15
<211> LENGTH: 33
<212> TYPE: DNA
<213> ORGANISM: Artificial Sequence
<220> FEATURE:
<223> OTHER INFORMATION: Primer cat-HindIII-F

<400> SEQUENCE: 15
ggcaagcttg agaaaaaaat cactggatat acc        33

<210> SEQ ID NO 16
<211> LENGTH: 29
<212> TYPE: DNA
<213> ORGANISM: Artificial Sequence
<220> FEATURE:
<223> OTHER INFORMATION: Primer cat-NdeI-R

<400> SEQUENCE: 16
ggccatatgt aagggcacca ataactgcc        29

<210> SEQ ID NO 17
<211> LENGTH: 33
<212> TYPE: DNA

<213> ORGANISM: Artificial Sequence
<220> FEATURE:
<223> OTHER INFORMATION: Primer TsLDC-SacI-F

<400> SEQUENCE: 17
ggcgagctca tggagaagca agagattaac aag           33

<210> SEQ ID NO 18
<211> LENGTH: 34
<212> TYPE: DNA
<213> ORGANISM: Artificial Sequence
<220> FEATURE:
<223> OTHER INFORMATION: Primer TsLDC-XbaI-R

<400> SEQUENCE: 18
ggctctagat tagaaatcgg ttacaacctg aatg          34

<210> SEQ ID NO 19
<211> LENGTH: 44
<212> TYPE: DNA
<213> ORGANISM: Artificial Sequence
<220> FEATURE:
<223> OTHER INFORMATION: Primer TsLDC-F

<400> SEQUENCE: 19
atttcacaca ggaaacagct atggagaagc aagagattaa caag     44

<210> SEQ ID NO 20
<211> LENGTH: 31
<212> TYPE: DNA
<213> ORGANISM: Artificial Sequence
<220> FEATURE:
<223> OTHER INFORMATION: Primer GkLDC-SacI-F

<400> SEQUENCE: 20
ggcgagctca tgtctcagct cgagacccct c             31

<210> SEQ ID NO 21
<211> LENGTH: 39
<212> TYPE: DNA
<213> ORGANISM: Artificial Sequence
<220> FEATURE:
<223> OTHER INFORMATION: Primer GkLDC-XbaI-R

<400> SEQUENCE: 21
ggctctagat taacgaattg gtttgtattc tttaatgac     39

<210> SEQ ID NO 22
<211> LENGTH: 42
<212> TYPE: DNA
<213> ORGANISM: Artificial Sequence
<220> FEATURE:
<223> OTHER INFORMATION: Primer GkLDC-F

<400> SEQUENCE: 22
atttcacaca ggaaacagct atgtctcagc tcgagacccc tc      42

<210> SEQ ID NO 23
<211> LENGTH: 29
<212> TYPE: DNA
<213> ORGANISM: Artificial Sequence
<220> FEATURE:
<223> OTHER INFORMATION: Primer TeLDC-SacI-F

<400> SEQUENCE: 23
ggcgagctca tggaacctct gctgcgtgc               29

<210> SEQ ID NO 24
<211> LENGTH: 32
<212> TYPE: DNA
<213> ORGANISM: Artificial Sequence
<220> FEATURE:
<223> OTHER INFORMATION: Primer TeLDC-XbaI-R

<400> SEQUENCE: 24
ggctctagat taaactttgc agatacgcag ag                              32

<210> SEQ ID NO 25
<211> LENGTH: 40
<212> TYPE: DNA
<213> ORGANISM: Artificial Sequence
<220> FEATURE:
<223> OTHER INFORMATION: Primer TeLDC-F

<400> SEQUENCE: 25
atttcacaca ggaaacagct atggaacctc tgctgcgtgc                      40

<210> SEQ ID NO 26
<211> LENGTH: 29
<212> TYPE: DNA
<213> ORGANISM: Artificial Sequence
<220> FEATURE:
<223> OTHER INFORMATION: Primer TrLDC-SacI-F

<400> SEQUENCE: 26
ggcgagctca tgtctgaaga acagcaacg                                  29

<210> SEQ ID NO 27
<211> LENGTH: 29
<212> TYPE: DNA
<213> ORGANISM: Artificial Sequence
<220> FEATURE:
<223> OTHER INFORMATION: Primer TrLDC-XbaI-R

<400> SEQUENCE: 27
ggctctagat taggcacgaa cgacacgga                                  29

<210> SEQ ID NO 28
<211> LENGTH: 40
<212> TYPE: DNA
<213> ORGANISM: Artificial Sequence
<220> FEATURE:
<223> OTHER INFORMATION: Primer TrLDC-F

<400> SEQUENCE: 28
atttcacaca ggaaacagct atgtctgaag aacagcaacg                      40

<210> SEQ ID NO 29
<211> LENGTH: 713
<212> TYPE: PRT
<213> ORGANISM: Escherichia coli

<400> SEQUENCE: 29

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu

```
                50                  55                  60
Asp Leu Cys Ser Asp Ile Asn Gln Leu Asn Glu Tyr Leu Pro Leu Tyr
 65                  70                  75                  80

Ala Phe Ile Asn Thr His Ser Thr Met Asp Val Ser Val Gln Asp Met
                 85                  90                  95

Arg Met Ala Leu Trp Phe Phe Glu Tyr Ala Leu Gly Gln Ala Glu Asp
                100                 105                 110

Ile Ala Ile Arg Met Arg Gln Tyr Thr Asp Glu Tyr Leu Asp Asn Ile
                115                 120                 125

Thr Pro Pro Phe Thr Lys Ala Leu Phe Thr Tyr Val Lys Glu Arg Lys
                130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
                180                 185                 190

His Thr Gly Pro His Leu Glu Ala Glu Glu Tyr Ile Ala Arg Thr Phe
                195                 200                 205

Gly Ala Glu Gln Ser Tyr Ile Val Thr Asn Gly Thr Ser Thr Ser Asn
                210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
                260                 265                 270

Gly Gly Ile Pro Arg Arg Glu Phe Thr Arg Asp Ser Ile Glu Glu Lys
                275                 280                 285

Val Ala Ala Thr Thr Gln Ala Gln Trp Pro Val His Ala Val Ile Thr
                290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
                340                 345                 350

Arg Val Ala Gly Lys Val Ile Phe Glu Thr Gln Ser Thr His Lys Met
                355                 360                 365

Leu Ala Ala Leu Ser Gln Ala Ser Leu Ile His Ile Lys Gly Glu Tyr
                370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
                420                 425                 430

Leu His Phe Arg Lys Glu Val Gln Arg Leu Arg Glu Glu Ser Asp Gly
                435                 440                 445

Trp Phe Phe Asp Ile Trp Gln Pro Gln Val Asp Glu Ala Glu Cys
                450                 455                 460

Trp Pro Val Ala Pro Gly Glu Gln Trp His Gly Phe Asn Asp Ala Asp
465                 470                 475                 480
```

-continued

```
Ala Asp His Met Phe Leu Asp Pro Val Lys Val Thr Ile Leu Thr Pro
                485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
            595                 600                 605

Ala Phe Asp Thr Leu Pro Glu Met Ile Met Thr Pro His Gln Ala Trp
        610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
            645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
            675                 680                 685

Phe Glu Thr Asp Ile His Gly Ala Lys Gln Asp Glu Asp Gly Val Tyr
            690                 695                 700

Arg Val Arg Val Leu Lys Met Ala Gly
705                 710
```

HETEROLOGOUS EXPRESSION OF THERMOPHILIC LYSINE DECARBOXYLASE AND USES THEREOF

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "55209_Seqlisting.txt." The Sequence Listing was created on Dec. 31, 2019, and is 43,358 bytes in size. The subject matter of the Sequence Listing is incorporated herein in its entirety by reference.

BACKGROUND OF THE INVENTION

The class of proteins known as acid decarboxylases is a group of enzymes that catalyze the decarboxylase reaction of basic amino acids (e.g., lysine, arginine, ornithine) in order to generate polyamines as part of the acid stress response in many microorganisms. Escherichia coli has several pyridoxal phosphate-dependent (PLP)-dependent) acid decarboxylases: CadA, LdcC, AdiA, SpeA, SpeC, SpeF, GadA, and GadB. All of these enzymes function within a narrow pH range, and the enzyme activity decreases significantly outside of that pH range (Kanjee et al., Biochemistry 50, 9388-9398, 2011). It has been previously observed that these PLP-dependent decarboxylases dimerize in order to form a complete active site. In some cases, such as CadA, the dimers form decamers that aggregate into higher molecular weight protein complexes required for optimal function. The inhibition of higher molecular weight protein complex formation (e.g., in conditions outside of the optimal pH) leads to a significant decrease in function (Kanjee et al., The EMBO Journal 30, 931-944, 2011).

The PLP-dependent decarboxylases that catalyze the conversion of lysine to cadaverine are called lysine decarboxylases (e.g., CadA, LdcC, and their homologs). Lysine decarboxylases are of particular interest, because cadaverine can be a platform chemical for the production of various products, such as 1,5-pentamethylene diisocyanate or polyamide 56. However, the production of cadaverine is harmful to the host cell, since cadaverine has been shown to be toxic to cells when present above a certain concentration (Qian et al., Biotechnol. Bioeng. 108, 93-103, 2011). Therefore, the control of lysine decarboxylase activity in the presence of lysine is an important factor to the over production of cadaverine at concentrations higher than that which can be tolerated by the host cell.

Prior art methods to control the activity of an enzyme that is toxic to a cell typically involve the use of inducible promoters to control the expression of the gene that encodes the enzyme. An ideal inducible promoter system exhibits no gene expression (and therefore no enzyme production and activity) in the absence of the inducer, and gene expression is turned ON only after the addition of the inducer. This inducible control provides a process that separates the growth phase of the cell from the production of an enzyme whose activity is harmful to the cell. The production of the harmful enzyme after the cell completes its growth phase reduces the toxic effect on the cell, since most toxic effects mainly inhibit cell growth and have less effect on cell function. In some scenarios, an inducible promoter has leaky expression, which means that there is a small amount of expression even in the absence of the inducer. Leaky expression is a problem if the cell is extremely sensitive to the toxic effect of the enzyme. For example, certain promoter systems, such as $P_{BAD}$, are known to have extremely low leaky expression, and are commonly used in the production of toxic genes (Qiu et al., Appl. Environ. Microbiol. 74, 7422-7426, 2008). Another commonly used inducible system with low leaky expression is the temperature-regulated promoter system, such as the pL or pR, that causes gene expression either by a relative increase or decrease in temperature (Valdez-Cruz et al., Microbial Cell Factories 9:18, 2010; Qoronfleh et al., J. Bacteriol. 174, 7902-7909, 1992). Temperature-controlled induction systems can also have low leaky expression as long as the temperature of the system is tightly controlled.

While previous research focused on controlling gene expression to control the activity of a toxic enzyme, there has been little work to directly control the activity of the toxic enzyme so that its presence even in the presence of its substrate does not affect cell growth.

BRIEF SUMMARY OF ASPECTS OF THE DISCLOSURE

This invention is based, in part, on methodology that provides direct control of the activity of a toxic enzyme, thus reducing toxicity even when the enzyme is produced in the presence of its substrate that is transformed into the toxic product. The compositions and methods described herein to directly control the activity of an enzyme in the presence of its substrate can also avoid the problems associated with leaky expression from a promoter. Furthermore, a control system of the present disclosure allows protein production to proceed normally during growth.

The lysine decarboxylases CadA and LdcC from Escherichia coli are mesophilic enzymes. Therefore, the stability and activity of the enzymes decrease significantly when the temperature is outside of the optimal temperature range for growth of E. coli (25° C. to 55° C.) (Lemmonier et al., Microbiology 144, 751-760, 1998). The present disclosure provide mesophilic microorganism (e.g., E. coli, C. glutamicum) that produce lysine and are genetically modified to express a lysine decarboxylase protein that has maximal activity when the temperature is greater than 55° C. or that has maximal activity when the temperature is lower than 20° C., thus providing lysine decarboxylase activity that is maximal at a temperature that is different from the growth temperature of the mesophilic microorganism and thereby decreases the toxic side-effects of the enzyme's activity on growth.

In some embodiments, the present disclosure provides a lysine production mesophilic microorganism (e.g., E. coli, C. glutamicum) genetically modified to express a lysine decarboxylase enzyme from a psychrophile, a microorganism that functions optimally below 20° C. Examples of psycrophiles include Carnobacterium pleistocenium, Trichococcus patagoniensis, and certain species of the genus Pseudomonas, Salmonella, Coliforms, Vibrio, and Listeria.

In some embodiments, the present disclosure provides a lysine production mesophilic microorganism (e.g., E. coli, C. glutamicum) genetically modified to express a lysine decarboxylase enzyme from a thermophile, a microorganism that functions optimally above 55° C. Examples of thermophiles include Aeropyrum pernix, Caldococcus litoralis; certain species of the genus Geobacillus, Gracilibacillus, Tepidanaerobacter, Thermosynechoccus, and Thermomicrobium; and certain species of the order Aquificales, Thermotogales, Sulfolobales, Thermoproteales, Desulfurococcales, Pyrodictiales, Thermococcales, Archaeoglobales, Methanococales, Methanobacteriales, and Methanopyrales.

In some embodiments, the present disclosure provide a thermophilic lysine production microorganism that is genetically modified to express a mesophilic enzyme, such as CadA or LdcC from *E. coli*, or a corresponding mesophilic lysine decarboxylase, such as CadA from *Klebsiella*, Enterobacteriaceae, or *Salmonella enterica*. Additional CadA polypeptides from other mesophilic species include *Serratia* sp., WP 033635725.1; and *Raoultella ornithinolytica*, YP 007874766.1. In some embodiments, a thermophilic host cell can be genetically modified to express a psychrophilic lysine decarboxylase enzyme. Once lysine production is complete in a thermophilic host modified to express a mesophilic lysine decarboxylase, the temperature can be adjusted to between 20° C. to 55° C. to turn ON lysine decarboxylase activity. In embodiments in which the thermophilic host is modified to express a psychrophilic lysine decarboxylase, once lysine production is complete, the temperature can be adjusted to below about 20° C. to increase lysine decarboxylase activity.

Similarly, in embodiments of the disclosure in which a psychrophile is the lysine production host, then a mesophilic enzyme such as *E. coli* CadA or LdcC, or a corresponding enzyme from another mesophilic host cell can be used as the protein switch for lysine decarboxylase activity. At the low temperatures required for optimal growth of psychrophile (<20° C.), the mesophilic enzyme would have low activity while lysine is being produced. Once lysine production is complete, then the temperature could be changed to a temperature between 20° C. to 55° C. to turn ON lysine decarboxylase activity. Similarly, a thermophilic enzyme in a psychrophilic host can also be used, where growth occurs below 20° C., and catalysis is conducted at a temperature above 55° C.

In a further aspect, the invention provides mesophilic host cell genetically modified to express a lysine decarboxylase from a thermophilic organism. In some embodiment, the lysine decarboxylase is from *Tepidanaerobacter syntrophicus, Geobacillus kaustophilus, Thermosynechoccus elongatus*, or *Thermomicrobium roseum*. In typical embodiments, the host cell is also genetically modified to over express one or more lysine biosynthesis polypeptides. In some embodiments, the mesophilic host cell is a bacterium. For example, in some embodiments, the host cell is from the genus *Escherichia, Hafnia*, or *Corynebacteria*. In some embodiments, the genetically modified host cell is *Escherichia coli*. In some embodiments, the genetically modified host cell is Hafnia *alvei*. In some embodiments, the genetically modified host cell is *Corynebacterium glutamicum*.

In an additional aspect, a culture of host cells modified in accordance with the invention can be employed to produce cadaverine. Thus, in some aspects, the method comprises culturing a mesophilic host cell that can produce lysine and is genetically modified to express a thermophilic lysine decarboxylase at a temperature of between about 20° C. to about 50° C., e.g., about 25° C. to about 42° C., for a period of time sufficient to produce lysine; followed by incubating the host cell and a temperature of above about 50° C., e.g., above about 55° C., but less than about 110° C. In some embodiments, the temperature is from about 55° C. to about 90° C.

In typical embodiments, the transition from the lysine production stage to the cadaverine production stage (i.e., the upshift in temperature that characterizes the cadaverine production stage relative to the lysine production stage) occurs after the cells finish log growth at the lower temperature (e.g., about 20° C. to about 50° C.; or about 25° C. to about 42° C.) and enter stationary phase. In some embodiments, the shift in temperature from the lower temperature to the higher temperature at which the thermophilic lysine decarboxylase is determined by the amount of glucose left in fermentation. In some embodiments to maximize productivity, the shift to the higher temperature takes place after glucose has been converted into lysine.

In one aspect, the invention thus provides a mesophilic microorganism host cell that produces lysine, and is genetically modified to express a thermophilic lysine decarboxylase and to overexpress one or more lysine biosynthesis polypeptides. In some embodiments, the host cell is genetically modified to comprise a synthetic operon polynucleotide that encodes the one or more lysine biosynthesis polypeptides. In some embodiments, the host cell is modified to overexpress at least six lysine biosynthesis polypeptides. In some embodiments, the host cell is genetically modified to comprise two or more synthetic operons comprising polynucleotides that encode the at least six lysine biosynthesis polypeptides. In some embodiments, the host cell is genetically modified to express exogenous *Streptomyces* lysC, *E. coli* dapAB, lysA, asd, aspC, and tetA polynucleotides to increase expression of lysine compared to the counterpart host cell that is not genetically modified to express the exogenous polynucleotides. In some embodiments, the thermophilic lysine decarboxylase has at least 70% amino acid sequence identity, or at least 80%, at least 85%, or at least 90% sequence identity to any one of SEQ ID NOS:1-4. In some embodiments, the thermophilic lysine decarboxylase has at least 95% amino acid sequence identity to any one of SEQ ID NOS:1-4. In other embodiments, the thermophilic lysine decarboxylase comprises the amino acid sequence of any one of SEQ ID NOS:1-4. In some embodiments, the mesophilic microorganism host cell is a bacterium. In some embodiments, the host cell is from the genus *Escherichia, Hafnia*, or *Corynebacteria*. Illustrative embodiments, the host cell is *Escherichia coli, Hafnia alvei*, or *Corynebacterium glutamicum*.

In a further aspect, the invention provides a method of producing cadaverine, the method comprising: (a) culturing a mesophilic microorganism host cell as set forth in the preceding paragraph, at a temperature from about 20° C. to about 50° C. for a time period sufficient to accumulate lysine; and (b) following step (a), incubating the culture of (a) at a temperature of above about 55° C. and less than about 110° C. In some embodiments, step (a) is performed at a temperature of from about 25° C. to about 45° C. In other embodiments, step (a) is performed at a temperature of from about 30° C. to about 40° C. In further embodiments, step (a) is performed at a temperature of from about 35° C. to about 39° C. In some embodiments, step (b) is performed at a temperature of from about 55° C. to about 90° C. In other embodiments, step (b) is performed at a temperature of from about 60° C. to about 75° C. In further embodiments step (b) is performed at a temperature of from about 60° C. to about 70° C.

In a further aspect, the invention provides a method of producing cadaverine, the method comprising incubating a lysine-containing composition with a thermophilic lysine decarboxylase in vitro in a reaction at a temperature of above about 55° C. and less than about 110° C. In some embodiments, the thermophilic lysine decarboxylase is expressed by a mesophilic microorganism. In some embodiments, the thermophilic lysine decarboxylase is immobilized to a solid support. In some embodiments, the thermophilic lysine decarboxylase has at least 70% amino acid sequence identity, or at least 80%, at least 85%, or at least 90% sequence identity to any one of SEQ ID NOS:1-4. In some embodiments, the thermophilic lysine decarboxylase has at least 95% amino acid sequence identity to any one of SEQ ID NOS:1-4. In other embodiments, the thermophilic lysine decarboxylase comprises the amino acid sequence of any one of SEQ ID NOS:1-4. In some embodiments, the temperature is above about 55° C. and less than about 90° C. In other embodiments, the temperature is from about 60° C. to about 75° C. In further embodiments, the temperature is from about 60° C. to about 70° C.

DESCRIPTION OF THE FIGURES

FIG. 1 shows a CLUSTAL O(1.2.4) multiple sequence alignment of *E. coli* LdcC and CadA polypeptide sequences with lysine decarboxylase polypeptide sequences from *Tepidanaerobacter syntrophicus* (SEQ ID NO:1, encoded by GenBank ID GAQ24853.1), *Geobacillus kaustophilus* (SEQ ID NO:2, encoded by GenBank ID BAD75350.1), *Thermosynechoccus elongatus* (SEQ ID NO:3, encoded by GenBank ID BAC09418.1), and *Thermomicrobium roseum* (SEQ ID NO:4, encoded by GenBank ID ACM05730.1.

DETAILED DESCRIPTION OF ASPECTS OF THE DISCLOSURE

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Terminology

As used in the context of the present disclosure, a "thermophilic lysine decarboxylase polypeptide" refers to a PLP-dependent lysine decarboxylase from a thermophile that catalyzes the decarboxylation of L-lysine to produce cadaverine. Thermophilic lysine decarboxylases function optimally at above about 55° C. Structural mechanisms contributing to thermostability are described, e.g., in Vieille & Zeikus *Microbiology and Molecular Biology Reviews*, 65(1), p. 1-43, 2001. Characteristic domains of thermophilic lysine decarboxylase polypeptides include a pyridoxal 5'-phosphate binding pocket and a conserved domain: OKR_DC_1_C (Orn/Lys/Arg decarboxylase, C-terminal domain; PFAM 03711; superfamily cl27246). Such enzymes are known in the art. Illustrative thermophilic lysine decarboxylases include *Tepidanaerobacter syntrophicus* lysine decarboxylase (GenBank Accession No. GAQ24853), *Geobacillus kaustophilus* lysine decarboxylase (GenBank Accession No. BAD75350), *Thermosynechoccus elongatus* lysine decarboxylase (GenBank Accession No. Accession No. BAC09418); *Thermomicrobium roseum* lysine decarboxylase (GenBank Accession No. ACM05730); *Geobacillus kaustophilis* lysine decarboxylase (GenBank Accession No. BAD74308); *Gracilibacillus halophiles* lysine decarboxylase (GenBank Accession No. ENH96106); *Geobacillus thermoleovorans* lysine decarboxylase (GenBank Accession No. AEV18557); *Ruminiclostridium thermocellus* lysine decarboxylase (GenBank Accession No. ADU75593); *Caldicellulosiruptor obsidians* lysine decarboxylase (GenBank Accession No. ADL43096); Parageobacillus genome sp. 1 lysine decarboxylase (GenBank Accession No. EZP77891); and *Anoxybacillus flavithermus* lysine decarboxylase (GenBank Accession No. EMT45272).

In some embodiments, a thermophilic lysine decarboxylase is from *Tepidanaerobacter syntrophicus, Geobacillus kaustophilus, Thermosynechoccus elongatus,* or *Thermomicrobium roseum*; or a biologically active variant of such a lysine decarboxylase enzyme. Biologically active variants include alleles, fragments, and interspecies homologs of the polypeptides. Illustrative thermophilic lysine decarboxylase polypeptide sequences include the lysine decarboxylase from *Tepidanaerobacter syntrophicus* (SEQ ID NO:1, encoded by GenBank ID GAQ24853.1), *Geobacillus kaustophilus* (SEQ ID NO:2, encoded by GenBank ID BAD75350.1), *Thermosynechoccus elongatus* (SEQ ID NO:3, encoded by GenBank ID BAC09418.1), and *Thermomicrobium roseum* (SEQ ID NO:4, encoded by GenBank ID ACM05730.1).

In some embodiments, a "thermophilic lysine decarboxylase polypeptide" has at least 60% amino acid sequence identity, typically at least 65%, 70%, 75%, 80%, 85%, 90% identity; often at least 91%, 92%, 93%, 94%, 95%, 96%, 97%, 98% or 99% or greater amino acid sequence identity, over a region of at least about 200, 300, or 400 or more amino acids to a naturally occurring thermophilic lysine decarboxylase polypeptide sequence. In some embodiments, a "thermophilic lysine decarboxylase polypeptide" has at least 90% identity; often at least 91%, 92%, 93%, 94%, 95%, 96%, 97%, 98% or 99% or greater, amino acid sequence identity to a naturally occurring thermophilic lysine decarboxylase polypeptide sequence over the length of the sequence. In some embodiments, a "thermophilic lysine decarboxylase polypeptide" has at least 60% amino acid sequence identity, often at least 65%, 70%, 75%, 80%, 85%, 90%, 91%, 92%, 93%, 94%, 95%, 96%, 97%, 98% or 99% or greater, amino acid sequence identity, over the length of the polypeptide of SEQ ID NO:1, SEQ ID NO:2, SEQ ID NO:3, or SEQ ID NO:4.

A "thermophilic lysine decarboxylase polynucleotide" as used herein refers to a polynucleotide that encodes a thermophilic lysine decarboxylase polypeptide as described in the previous paragraph. A nucleic acid or polynucleotide that encodes a thermophilic lysine decarboxylase polypeptide refers to a gene, pre-mRNA, mRNA, and the like, including nucleic acids encoding variants, alleles, and fragments. Illustrative nucleic acid sequences encoding the thermophilic lysine decarboxylase polypeptide sequences of SEQ ID NOS:1, 2, 3, and 4 are provided in SEQ ID NOS:5, 6, 7, and 8, respectively.

The term "enhanced" or "improved" in the context of the production of an amino acid derivative, e.g., cadaverine, as used herein refers to an increase in the production of the amino acid derivative produced by a genetically modified mesophilic microorganism, which microorganism is modified to express a thermophilic lysine decarboxylase as described herein, at a temperature of about 50° C., but less than about 110° C. in comparison to a control counterpart microorganism of the same strain that is not modified to express the thermophilic lysine decarboxylase. In some embodiments, the control counterpart microorganism is of the same strain, but is modified to overexpress a mesophilic lysine decarboxylase compared to the strain modified to express the thermophilic lysine decarboxylase. In one embodiment, production of the amino acid derivative, e.g., cadaverine, by the genetically modified microorganism is improved by at least 10%, 15% 20%, 30%, 40%, 50%, 60%, 70%, 80%, 90%, 100%, 125%, 150%, 200% or greater, compared to the control. An increase in production can be assessed by measuring the production of the amino acid derivative, e.g., cadaverine, by the mesophilic host cell modified to express a thermophilic lysine decarboxylase and the control cell under identical conditions that include incubation of the culture, or an extract of the cultured cells, at a temperature of about 50° C. and less than about 110° C., for example, for a period of time of at least one hour, e.g., two, three, four, five or six hours. By way of illustration, in some embodiments, production of the amino acid derivative, e.g., cadaverine, is tested by culturing mesophilic host cells modified to express a thermophilic lysine decarboxylase under mesophilic conditions (e.g., at 30° to 40° C.) in comparison to a control cell of the same strain modified to express a mesophilic lysine decarboxylase for a period of time, e.g., overnight, sufficient to produce lysine. The host cells are then lysed. Aliquots of supernatant from the lysed cells are incubated at a thermophilic temperature, e.g., 65° C., for four hours with lysine-HCl and PLP to a final concentration of 160 g/L and 0.1 mM. Cadaverine production from the cell lysates from the control cells and the cells modified to express the thermophilic lysine decarboxylase can then be measured and compared. An exemplary assay is provided in the Examples section.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a position of a variant thermophilic lysine decarboxylase polypeptide sequence "corresponds to" a position in reference polypeptide sequence SEQ ID NO:1 (or in a position of a reference polypeptide sequence of SEQ ID NO:2, 3, 4, or 9) when the variant polypeptide is aligned with the reference polypeptide sequence in a maximal alignment.

The terms "wild type", "native", and "naturally occurring" with respect to a thermophilic lysine decarboxylase polypeptide are used herein to refer to a thermophilic lysine decarboxylase protein that has a sequence that occurs in nature.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of this disclosure for two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether a thermophilic lysine decarboxylase polypeptide has sequence identity to any one of SEQ ID NO:1, SEQ ID NO:2, SEQ ID NO:3, or SEQ ID NO:4, is the BLAST algorithm, which is described in Altschul et al., 1990, J. Mol. Biol. 215:403-410). Software for performing BLAST analyses is publicly available through the National Center for Biotechnology Information (on the worldwide web at ncbi.nlm.nih.gov/). Illustrative software for performing protein sequence alignments include ClustalW2 and BLASTP. For amino acid sequences, the BLASTP program uses as defaults a word size (W) of 3, an expect threshold (E) of 10, and the BLOSUM62 scoring matrix (see Henikoff & Henikoff, Proc. Natl. Acad. Sci. USA 89:10915 (1989)). In the present disclosure, polypeptide sequence identity is typically determined using BLASTP Align Sequence with the default parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Optimal alignments are typically conducted using BLASTP with default parameters.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

The term "polypeptide" as used herein includes reference to polypeptides containing naturally occurring amino acids and amino acid backbones as well as non-naturally occurring amino acids and amino acid analogs.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)). In some embodiments, conservative substitutions are employed in generating Cada variants having substitutions at sites other than a glutamate residue.

The term "promoter," as used herein, refers to a polynucleotide sequence capable of driving transcription of a nucleic acid sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different species). Similarly, a polypeptide is "heterologous" to a host cell if the native wildtype host cell does not produce the polypeptide.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of a plasmid or vector encoding that sequence, such as to overexpress or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence can have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, may refer to a polypeptide molecule that is free of other components of the cell, i.e., it is not associated with in vivo cellular substances.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2016).

Summary of Certain Aspects of the Disclosure

In one aspect, the invention provides a genetically modified mesophilic host cell that is modified to express a thermophilic lysine decarboxylase. In some embodiments, the thermophilic lysine decarboxylase of SEQ ID NO:1, 2, 3, or 4; or a thereof as described herein.

Thermophilic Lysine Decarboxylase Polypeptide

Thermophilic lysine decarboxylase enzymes are known and are part of a well-characterized family of decarboxylases as described above. Lysine decarboxylase polypeptides from four thermophilic microorganisms of very different genetic backgrounds are provided by way of illustration of the present invention. The four illustrative thermophiles are *Tepidanaerobacter syntrophicus* (GenBank ID GAQ24853.1), *Geobacillus kaustophilus* (GenBank ID BAD75350.1), *Thermosynechoccus elongatus* (GenBank ID BAC09418.1), and *Thermomicrobium roseum* (GenBank ID ACM05730.1). Polypeptide sequences encoded by the genes are provided in SEQ ID NOS 1, 2, 3, and 4, respectively. The protein sequence alignment of the lysine decarboxylase enzymes from these four thermophiles and with CadA and LdcC from *E. coli* show little similarity in protein sequence (FIG. 1). While *E. coli* CadA and LdcC share 69% sequence identity, the sequence identity between the four thermophilic lysine decarboxylases, CadA, and LdcC range from 23.61% to 38.44%. The thermophilic lysine decarboxylase protein sequences are also significantly shorter than their mesophilic counterparts. The illustrative thermophilic lysine decarboxylases are between 420 and 500 amino acids in length, whereas the mesophilic lysine decarboxylases are over 700 amino acids in length.

Despite the low overall sequence identity shared between these six proteins and their differences in size, there are conserved domains and structural motifs. First, the conserved lysine residue at amino acid position 367 (as determined with the *E. coli* CadA polypeptide sequence (SEQ ID NO:9) found in mesophilic lysine decarboxylases is conserved. Further, four of the seven residues important for binding PLP in the mesophilic enzymes are also conserved in the four thermophilic enzymes: S364, H366, T398, S400. In addition, two of the seven amino acid residues important for binding PLP (S221 and T399) have either serine or threonine in the corresponding position in the thermophilic enzymes. The last of the seven amino acid residues important for binding PLP (T220) also has an alanine, serine, or threonine in the thermophilic enzymes. Furthermore, of the three residues important for enhancing the electron withdrawing ability of PLP, two are conserved—D330 and H245. W333, although not conserved, is replaced with amino acids with similar polar strengths—tryptophan, glutamine, or methionine in the thermophilic polypeptide sequences. Thus, despite the significant difference in the sizes of the thermophilic and mesophilic enzymes, there is a high degree of conservation in active site residues. Amino acid residues, such as R206, R558, R565, and R568, that are important for ppGpp inhibition of CadA are not conserved in the thermophilic enzymes, which indicates that the thermophilic counterparts are not inhibited by the alarmone ppGpp.

In some embodiments, a variant thermophilic lysine decarboxylase that is expressed in a mesophilic host cell in accordance with the invention comprises conserved or semi-conserved residues described in the preceding paragraph (T220, S221, H245, D330, W333, S364, H366, K367, T398, T399, and S400 of SEQ ID NO:9, which correspond to amino acids A94, T95, H119, D199, Q202, S226, H228, K229, T261, S262, and S263 of SEQ ID NO:1, respectively) and has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of 400 or more amino acids in length, or over the length of, the polypeptide of SEQ ID NO:1.

In some embodiments, a variant thermophilic lysine decarboxylase that is expressed in a mesophilic host cell in accordance with the invention comprises conserved or semi-conserved residues described above (T220, S221, H245, D330, W333, S364, H366, K367, T398, T399, and S400 of SEQ ID NO:9, which correspond to amino acids T90, S91, H115, D195, H198, S223, H225, K226, T258, T259, and S260 of SEQ ID NO:2, respectively) and has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of 400 or more amino acids in length, or over the length of, the polypeptide of SEQ ID NO:2.

In some embodiments, a variant thermophilic lysine decarboxylase that is expressed in a mesophilic host cell in accordance with the invention comprises conserved or semi-conserved residues described above (T220, S221, H245, D330, W333, S364, H366, K367, T398, T399, and S400 of SEQ ID NO:9, which correspond to amino acids A56, T57, H81, D161, H164, S189, H191, K192, T224, S225, and S226 of SEQ ID NO:3, respectively) and has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of 400 or more amino acids in length, or over the length of, the polypeptide of SEQ ID NO:3.

In some embodiments, a variant thermophilic lysine decarboxylase that is expressed in a mesophilic host cell in accordance with the invention comprises conserved or semi-conserved residues described above (T220, S221, H245, D330, W333, S364, H366, K367, T398, T399, and S400 of SEQ ID NO:9, which correspond to amino acids S92, T93, H117, D197, W200, S225, H227, K228, T260, T261, and S262 of SEQ ID NO:4, respectively) and has at least 60% amino acid sequence identity, often at least 65%, 70%, 75%, 80%, or 85% identity; and typically at least 90%, 91%, 92%, 93%, 94%, 95%, 96%, 97%, 98% or 99% or greater amino acid sequence identity, over a region of 400 or more amino acids in length, or over the length of, the polypeptide of SEQ ID NO:4.

Nucleic Acids Encoding Thermophilic Lysine Decarboxylase Polypeptides

Isolation or generation of thermophilic lysine decarboxylase polynucleotide sequences can be accomplished by a number of techniques. In some embodiments, oligonucleotide probes and based on the sequences disclosed here can be used to identify the desired polynucleotide in a cDNA or genomic DNA library from a desired bacteria species. For generation of variants of thermophilic lysine decarboxylase polypeptides, desired substitutions may be introduced into a polynucleotide sequence encoding a native thermophilic lysine decarboxylase sequence using appropriate primers.

Appropriate primers and probes for identifying a lysine decarboxylase polynucleotide in a thermophilic microorganism can be generated from comparisons of the sequences provided herein or generated based on a CadA polynucleotide sequence from another bacteria. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding a thermophilic lysine decarboxylase polypeptide for use in the disclosure includes genes and gene products identified and characterized by techniques such as hybridization and/or sequence analysis using illustrative nucleic acid sequences, e.g., a thermophilic lysine decarboxylase polynucleotide sequence of any one of SEQ ID NOS:5-8. In some embodiments, a host cell is genetically modified by introducing a nucleic acid sequence having at least 60% identity, or at least 70%, 75%, 80%, 85%, or 90% identity, or 95% identity, or greater, to an thermophilic lysine decarboxylase polynucleotide of any one of SEQ ID NOS:5-8.

Nucleic acid sequences encoding a thermophilic lysine decarboxylase in accordance with the invention may additionally be codon-optimized for expression in a desired mesophilic host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; *Nucleic Acids Res.* 20:2111-2118; Nakamura et al., 2000, *Nucl. Acids Res.* 28:292). Illustrative codon-optimized nucleic sequences encoding the polypeptides of SEQ ID NOS:1-4 are provided in SEQ ID NOS:5-8, respectively.

Thermophiles that are employed as a source of thermophile lysine decarboxylase sequences for use in the invention can be any thermophilic microorganism, including, but not limited to, the thermophiles *Aeropyrum pernix, Caldococcus litoralis*; thermophilic species of the genus *Pyrococcus, Geobacillus, Gracilibacillus, Tepidanaerobacter, Thermosynechoccus*, and *Thermomicrobium*; and thermophilic species of the order Aquificales, Thermotogales, Sulfolobales, Thermoproteales, Desulfurococcales, Pyrodictiales, Thermococcales, Archaeoglobales, Methanococales, Methanobacteriales, and Methanopyrales.

Preparation of Recombinant Vectors

Recombinant vectors for expression of a thermophilic lysine decarboxylase protein can be prepared using methods well known in the art. For example, a DNA sequence encoding a thermophilic lysine decarboxylase, can be combined with transcriptional and other regulatory sequences which will direct the transcription of the sequence from the gene in the intended mesophilic host cells, e.g., bacterial cells such as *H. alvei, E. coli*, or *C. glutamicum*. In some embodiments, an expression vector that comprises an expression cassette that comprises the gene encoding the thermophilic lysine decarboxylase polypeptide further comprises a promoter operably linked to the nucleic acid sequence encoding the polypeptide. In other embodiments, a promoter and/or other regulatory elements that direct transcription of the a thermophilic lysine decarboxylase polynucleotide encoding the lysine decarboxylase polypeptide are endogenous to the host cell and an expression cassette comprising the gene is introduced, e.g., by homologous recombination, such that the exogenous gene is operably linked to an endogenous promoter and expression is driven by the endogenous promoter.

As noted above, expression of the polynucleotide encoding a thermophilic lysine decarboxylase variant polypeptide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., arabinose, xylose, rhamnose, galactose and maltose. Additional examples include promoters such as the trp promoter, bla promoter, bacteriophage lambda PL, tet promoter and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, *Appl. Environ. Microbiol.* 64:82, 1998; Shimada, et al., *J. Bacteriol.* 186:7112, 2004; and Miksch et al., *Appl. Microbiol. Biotechnol.* 69:312, 2005.

An expression vector may also comprise additional sequences that influence expression of a polynucleotide encoding a thermophilic lysine decarboxylase polypeptide. Such sequences include enhancer sequences, a ribosome binding site, or other sequences such as transcription termination sequences, and the like.

A vector expressing a polynucleotide encoding a thermophilic lysine decarboxylase polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli, H. alvei*, or *C. glutamicum*.

Although any suitable expression vector may be used to incorporate the desired sequences, readily available bacterial expression vectors include, without limitation: plasmids such as pSClOl, pBR322, pBBRlMCS-3, pUR, pET, pEX, pMRlOO, pCR4, pBAD24, p15a, pACYC, pUC, e.g., pUC18 or pUC19, or plasmids derived from these plasmids; and bacteriophages, such as M13 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified mesophilic host cell that is engineered to express a thermophilic lysine decarboxylase polypeptide. A genetically modified mesophilic host strain of the present invention typically comprises at least one additional genetic modification to enhance production of an amino acid or amino acid derivative relative to a control strain that does not have the one additional genetic modification, e.g., a wildtype strain or a cell of the same strain without the one additional genetic modification. An "additional genetic modification to enhance production of an amino acid or amino acid derivative" can be any genetic modification. In some embodiments, the genetic modification is the introduction of a polynucleotide that expresses an enzyme involved in the synthesis of the amino acid or amino acid derivative. In some embodiments, the host cell comprises multiple modifications to increase production, relative to a wildtype host cell, of an amino acid or amino acid derivative.

In some aspects, genetic modification of a mesophilic host cell to express a thermophilic lysine decarboxylase polypeptide is performed in conjunction with modifying the host cell to overexpress one or more lysine biosynthesis polypeptides. The term "overexpression" in this context is used herein to refer to an increase in the amount of lysine biosynthesis polypeptide in a genetically modified cell, e.g., a cell into which an expression construct encoding a lysine biosynthesis polypeptide has been introduced, compared to the amount of polypeptide in a counterpart cell that does not have the genetic modification, i.e., a cell of the same strain without the modification. An increased level of expression is typically at least 5%, or at least 10%, 20%, 30%, 40%, 50%, 60%, 70%, 80%, 90%, 100%, or greater, compared to the counterpart unmodified cell. The unmodified cell need not express the polypeptide. Thus, the term "overexpression" also includes embodiments in which a polypeptide is expressed in a host cell that does not natively express the polypeptide. Increased expression of a polypeptide can be assessed by any number of assays, including, but not limited to, measuring the level of RNA transcribed from the gene encoding the polypeptide, the level of polypeptide, and/or the level of polypeptide activity.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
|---|---|---|---|
| α-ketoglutarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/ 2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate: meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

| Protein | Gene | EC Number | GenBank Accession No. |
|---|---|---|---|
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |

-continued

| Protein | Gene | EC Number | GenBank Accession No. |
|---|---|---|---|
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/1.1.1.3 | NP_414543 |

Nucleic acids encoding a lysine biosynthesis polypeptide may be introduced into the host cell along with a polynucleotide encoding a thermophilic lysine decarboxylase polypeptide, e.g., encoded on a single expression vector, or introduced in multiple expression vectors at the same time. Alternatively, the host cell may be genetically modified to overexpress one or more lysine biosynthesis polypeptides before or after the host cell is genetically modified to express a thermophilic lysine decarboxylase polypeptide.

In some embodiments, a mesophilic host cell that is engineered to express a thermophilic lysine decarboxylase is engineered to express one or more lysine synthetic operons comprising multiple genes that encode protein for lysine production. Such genes can be incorporated into more than one synthetic operon, e.g., each operon may comprise about 3 kb in length. Thus, for example, and illustrative lysine synthetic operons (I and II) can include six genes, such as *Streptomyces* lysC, *E. coli* dapAB, lysA, asd, aspC, and tetA nucleic acid sequences, where each operon comprises three genes.

A host cell engineered to express a thermophilic lysine decarboxylase polypeptide is typically a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella,* or *Klebsiella* taxonomical classes. In some embodiments, the host cells are members of the genus *Escherichia, Hafnia,* or *Corynebacterium*. In some embodiments, the host cell is an *Escherichia coli, Hafnia alvei,* or *Corynebacterium glutamicum* host cell. In some embodiments, the host cell is *Escherichia coli*. In some embodiments, the host cell is *Hafnia alvei*. In some embodiments, the host cell is *Corynebacterium glutamicum*.

In some embodiments, the host cell is a gram-positive bacterial host cell, such as a *Bacillus* sp., e.g., *Bacillus subtilis* or *Bacillus licheniformis*; or another *Bacillus* sp. such as *B. alcalophilus, B. aminovorans, B. amyloliquefaciens, B. caldolyticus, B. circulans, B. stearothermophilus, B. thermoglucosidasius, B. thuringiensis* or *B. vulgatis*.

Host cells modified in accordance with the invention can be screened for increased production of lysine or a lysine derivative, such as cadaverine, as described herein.

In some embodiments, a thermophilic lysine decarboxylase polypeptide may be recovered from a host cell that expresses the variant polypeptide. In some embodiments, the recovered variant protein may be immobilized onto a solid substrate or inert material.

Methods of Producing a Lysine Derivative.

As used herein, the terms "about" when used to modify a numeric value in a temperature range indicates that the numeric value as reasonable deviations from the value e.g., within 1° or 2° below or above the value recited in the range, are within the intended meaning of the recited value or range.

A mesophilic host cell genetically modified to express a thermophilic lysine decarboxylase polypeptide can be employed to produce lysine or a derivative of lysine, such as cadaverine. To produce cadaverine, a host cell genetically modified to express a thermophilic lysine decarboxylase polypeptide as described herein can be cultured under conditions suitable to allow expression of the polypeptide and expression of genes that encode the enzymes that are used to produce lysine. Culture of the mesophilic host cell to produce lysine is conducted at a temperature that is suitable for growth of mesophilic host cells. In some embodiments, the mesophilic host cell is cultured at a temperature from about 20° C. to about 50° C. In some embodiments, the host is cultured at a temperature of from about 25° C. to about 45° C. In some embodiments, the mesophilic host cell is cultured at a temperature of from about 30° C. to about 42° C. or from about 30° C. to about 40° C. The host cell is typically cultured at the temperature that is suitable to produce lysine for a time period sufficient such that lysine production is complete. In typical embodiments, the cells are allowed to grow until stationary phase at which point the amount of glucose in the medium may be monitored. The culture is then shifted at the desired time, e.g., when glucose is minimally detected, to a higher temperature at which the thermophilic lysine decarboxylase is active.

As describe above, culture of the genetically modified host cell at a temperature suitable for growth of a mesophile to produce lysine is then followed by incubation of the host cells at a temperature at which the thermophilic lysine decarboxylase is active, e.g., at a temperature of above about 55° C., but less than about 110° C. In some embodiments, the cells are cultured at a temperature ranging from above about 55° C. to about 90° C. In some embodiments, the cells are cultured at a temperature ranging from about 60° C. to about 70° C.

Culture of the mesophilic host cell modified in accordance with the invention at a lower temperature suitable for mesophilic cell growth for a time period sufficient to accumulate lysine followed by culture at a temperature suitable to support activity of the thermophilic lysine decarboxylase expressed by the host cells improves lysine production, e.g., by reducing toxic side effects of lysine decarboxylase activity on cell growth.

Host cells may be cultured using well known techniques (see, e.g., the illustrative conditions provided in the examples section.)

In some embodiments, host cells are cultured using nitrogen sources that are not salts (e.g., ammonium sulfate or ammonium chloride), such as ammonia or urea.

The lysine or lysine derivative then be separated and purified using known techniques. Lysine or lysine derivatives, e.g., cadverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples. The following examples are offered for illustrative purposes, and are not intended to limit the invention in any manner. Those of skill in the art will

EXAMPLES

Example 1: Construction of Plasmid Vectors that Encode CadA

A plasmid vector containing wild-type *E. coli* cadA (SEQ ID NO:10), which encodes the lysine decarboxylase CadA (SEQ ID NO:9), was amplified from the *E. coli* MG1655 K12 genomic DNA using the PCR primers cadA-F and cadA-R, digested using the restriction enzymes SacI and XbaI, and ligated into pUC18 to generate the plasmid pCIB60. The 5' sequence upstream of the cadA gene was optimized using the PCR primers cadA-F2 and cadA-R2 to create pCIB71. The chloramphenicol resistance gene cat was amplified using the primers cat-HindIII-F and cat-NdeI-R, and cloned behind cadA in pCIB71 to create pCIB128.

Example 2: Construction of a Plasmid Vector Expressing a Lysine Decarboxylase Polypeptide from *Tepidanaerobacter syntrophicus*

The amino acid sequence of lysine decarboxylase from *T. syntrophicus* (TsLDC) was obtained from NCBI (GenBank ID GAQ24853.1). The nucleic acid encoding TsLDC was codon optimized (SEQ ID NO:5) for heterologous expression of the protein (SEQ ID NO:1) in *E. coli*. Codon optimization and DNA assembly was performed according to Hoover D M & Lubkowski J, *Nucleic Acids Research* 30:10, 2002. The synthesized DNA product was amplified with the PCR primers TsLDC-SacI-F and TsLDC-XbaI-R, digested using the restriction enzymes SacI and XbaI, and ligated into pUC18. The 5' sequence upstream of the TsLDC gene was optimized using the PCR primers TsLDC-F and cadA-R2 to create plasmid pCIB370.

Example 3: Construction of a Plasmid Vector Expressing a Lysine Decarboxylase Polypeptide from *Geobacillus kaustophilus*

The amino acid sequence of lysine decarboxylase from *G. kaustophilus* (GkLDC) was obtained from NCBI (GenBank ID BAD75350.1). The nucleic acid sequence encoding GkLDC sequence was codon optimized (SEQ ID NO:6) for heterologous expression of the protein (SEQ ID NO:2) in *E. coli*. Codon optimization and DNA assembly was performed according to Hoover D M & Lubkowski J, *Nucleic Acids Research* 30:10, 2002. The synthesized DNA product was amplified with the PCR primers GkLDC-SacI-F and GkLDC-XbaI-R, digested using the restriction enzymes SacI and XbaI, and ligated into pUC18. The 5' sequence upstream of the GkLDC gene was optimized using the PCR primers GkLDC-F and cadA-R2 to create plasmid pCIB371.

Example 4: Construction of a Plasmid Vector Expressing a Lysine Decarboxylase Polypeptide from *Thermosynechoccus elongatus*

The amino acid sequence of lysine decarboxylase from *T. elongatus* (TeLDC) was obtained from NCBI (GenBank ID BAC09418.1). The nucleic acid sequence encoding TeLDC sequence was codon optimized (SEQ ID NO:7) for heterologous expression of the protein (SEQ ID NO:3 in *E. coli*. Codon optimization and DNA assembly was performed according to Hoover D M & Lubkowski J, *Nucleic Acids Research* 30:10, 2002. The synthesized DNA product was amplified with the PCR primers TeLDC-SacI-F and TeLDC-XbaI-R, digested using the restriction enzymes SacI and XbaI, and ligated into pUC18. The 5' sequence upstream of the TeLDC gene was optimized using the PCR primers TeLDC-F and cadA-R2 to create plasmid pCIB372.

Example 5: Construction of a Plasmid Vector Expressing a Lysine Decarboxylase Polypeptide from *Thermomicrobium roseum*

The amino acid sequence of lysine decarboxylase from *T. roseum* (TrLDC) was obtained from NCBI (GenBank ID ACM05730.1). The nucleic acid sequence encoding TrLDC was codon optimized (SEQ ID NO:8) for heterologous expression of the protein (SEQ ID NO:4) in *E. coli*. Codon optimization and DNA assembly was performed according to Hoover D M & Lubkowski J, *Nucleic Acids Research* 30:10, 2002. The synthesized DNA product was amplified with the PCR primers TrLDC-SacI-F and TrLDC-XbaI-R, digested using the restriction enzymes SacI and XbaI, and ligated into pUC18. The 5' sequence upstream of the TrLDC gene was optimized using the PCR primers TrLDC-F and cadA-R2 to create plasmid pCIB373.

Example 6: Comparison of Lysine Decarboxylase Activity at 37° C. and 65° C.

*E. coli* BL21 was transformed with the plasmids pCIB71, pCIB370, pCIB371, pCIB372, or pCIB373. A single colony from each transformation was grown overnight at 37° C. in 100 mL of LB medium with carbenicillin (100 µg/mL). The following day, each sample was lysed with a french press. The lysed samples were centrifuged, and the supernatant was separated from the pellet in order to perform in vitro experiments. Equal amounts of enzyme from each sample were incubated at either 37° C. or 65° C. for 4 hours with lysine-HCl and PLP to a final concentration of 160 g/L and 0.1 mM, respectively. Cadaverine production from each sample was quantified using NMR, and yield was calculated by dividing the molar amount of cadaverine produced by the molar amount of lysine added. The yield from each sample is presented in Table 1.

TABLE 1

Production of cadaverine by lysine decarboxylases from *E. coli*, *T. syntrophicus*, *G. kaustophilus*, *T. elongates*, and *T. roseum*.

| Strain | Plasmid | Enzyme | Cadaverine Yield (%) | |
|---|---|---|---|---|
| | | | 37° C. | 65° C. |
| *E. coli* BL21 | pCIB71 | CadA | 60.0 ± 2.2 | 10.0 ± 4.3 |
| | pCIB370 | TsLDC | 5.2 ± 3.1 | 30.8 ± 3.7 |
| | pCIB371 | GkLDC | 7.9 ± 2.4 | 35.2 ± 5.2 |
| | pCIB372 | TeLDC | 6.1 ± 1.9 | 28.1 ± 4.7 |
| | pCIB373 | TrLDC | 3.0 ± 1.2 | 40.3 ± 3.6 |

Table 1 shows that wild-type mesophilic lysine decarboxylase CadA (pCIB71) shows significantly higher activity at 37° C. compared to 65° C. However, the plasmids harboring lysine decarboxylase from thermophilic microorganisms (pCIB370-373) show higher activity at 65° C. compared to 37° C. Even though the activity of the thermophilic lysine decarboxylase at 65° C. is not as high as the activity of the mesophilic lysine decarboxylase at 37° C., the activity is still higher than that of the mesophilic enzyme at 65° C.

Example 7: Comparison of Lysine Decarboxylase Stability at 37° C. and 65° C.

The activities of lysine decarboxylases were determined following incubation for different periods of time at 37° C. and 65° C., in order to determine whether the enzymes are able to maintain the structural integrity at different temperatures necessary for function. *E. coli* BL21 was transformed with the plasmids pCIB71, pCIB370, pCIB371, pCIB372, or pCIB373. A single colony from each transformation were grown overnight at 37° C. in 100 mL of LB medium with carbenicillin (100 μg/mL). The following day, each sample was lysed with a french press. The lysed samples were centrifuged, and the supernatant was separated from the pellet in order to perform in vitro experiments. Equal amounts of enzyme from each sample were incubated at 37° C. for 20, 30, and 40 hours. After incubation at the specific temperature and for the specific time period, the samples were incubated at either 37° C. or 65° C. for 4 hours with lysine-HCl and PLP to a final concentration of 160 g/L and 0.1 mM, respectively. Cadaverine production from each sample was quantified using NMR, and yield was calculated by dividing the molar amount of cadaverine produced by the molar amount of lysine added. The yield from each sample is presented in Table 2.

TABLE 2

Production of cadaverine by different lysine decarboxylases following incubation at 37° C. for different amounts of time.

| | | | Reaction | Incubation Time (h) | | | |
|---|---|---|---|---|---|---|---|
| Strain | Plasmid | Enzyme | Temp (° C.) | 0 | 20 | 30 | 40 |
| *E. coli* BL21 | pCIB71 | CadA | 37 | 60 | 42 | 37 | 25 |
| | | | 65 | 10 | 7 | 5 | 4 |
| | pCIB370 | TsLDC | 37 | 5 | 7 | 6 | 5 |
| | | | 65 | 31 | 30 | 28 | 29 |
| | pCIB371 | GkLDC | 37 | 8 | 6 | 4 | 5 |
| | | | 65 | 35 | 33 | 33 | 30 |
| | pCIB372 | TeLDC | 37 | 6 | 7 | 5 | 5 |
| | | | 65 | 28 | 28 | 29 | 27 |
| | pCIB373 | TrLDC | 37 | 3 | 5 | 4 | 3 |
| | | | 65 | 40 | 39 | 39 | 37 |

Table 2 shows that mesophilic CadA stability at 37° C. is the lowest out of the six proteins tested. Its activity at 37° C. decreased by more than 50% after incubation for 40 hours. Its activity at 65° C. also decreased significantly compared to that at 37° C. The lysine decarboxylases from thermophilic microorganisms all show little activity at 37° C., similar to CadA activity at 65° C. However, the lysine decarboxylases from thermophilic microorganisms all show relatively stable activity at 65° C. even after 40 hours of incubation at 37° C. This suggests that production and maintenance of the lysine decarboxylases from thermophilic microorganisms can be performed at 37° C. without much effect on its activity at 65° C.

Example 8: Production of Cadaverine from *E. coli* Co-Overexpressing Genes that Encode a Thermophilic Lysine Decarboxylase, and the Lysine Synthetic Operons I and II at 37° C.

CIB103-3 (FROM MODIFIED MEMBRANE PERMEABILITY PCT/CN2015/094121 OR WO2017079872A1) was transformed with pCIB71, pCIB370, pCIB371, pCIB372, or pCIB373. Three single colonies from each transformation were grown overnight at 37° C. in 4 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 μg/mL), and carbenicillin (100 μg/mL). The following day, each culture was inoculated into 50 mL of fresh medium with 0.7% $CaCO_3$ and grown for 72 hours at 37° C., at which point the concentrations of lysine and cadaverine in each culture were determined (Table 3).

TABLE 3

Production of lysine and cadaverine by *E. coli* strains containing Synthetic Operons I and II, and co-producing lysine decarboxylases at 37° C.

| Plasmids | Protein(s) | Lysine (g/L) | Cadaverine (g/L) |
|---|---|---|---|
| pCIB103-3 | S-LysC, DapA, LysA, Asd, DapB, AspC, TetA | 6.3 ± 0.1 | N.D. |
| pCIB103-3, pCIB71 | S-LysC, DapA, LysA, Asd, DapB, AspC, TetA, CadA | 0.4 ± 0.2 | 5.7 ± 0.2 |
| pCIB103-3, pCIB370 | S-LysC, DapA, LysA, Asd, DapB, AspC, TetA, TsLDC | 5.9 ± 0.1 | N.D. |
| pCIB103-3, pCIB371 | S-LysC, DapA, LysA, Asd, DapB, AspC, TetA, GkLDC | 6.0 ± 0.2 | 0.8 ± 0.3 |
| pCIB103-3, pCIB372 | S-LysC, DapA, LysA, Asd, DapB, AspC, TetA, TeLDC | 6.1 ± 0.3 | 0.5 ± 0.2 |
| pCIB103-3, pCIB373 | S-LysC, DapA, LysA, Asd, DapB, AspC, TetA, TrLDC | 6.0 ± 0.2 | N.D. |

As shown in Table 3, the overexpression of the mesophilic lysine decarboxylase CadA (pCIB103-3, pCIB71) in a host able to produce lysine leads to the production of cadaverine with trace amounts of lysine when the host cell is grown at 37° C. The overexpression of the thermophilic lysine decarboxylases (pCIB103-3, pCIB370-373) leads to lysine accumulation with little to no cadaverine produced, like the control host that does not overexpress any lysine decarboxylase (pCIB103-3).

Example 9: Production of Cadaverine from *E. coli* Co-Overexpressing Genes that Encode a Thermophilic Lysine Decarboxylase, and the Lysine Synthetic Operons I and II at 65° C.

CIB103-3 was transformed with pCIB71, pCIB370, pCIB371, pCIB372, or pCIB373. Three single colonies from each transformation were grown overnight at 37° C. in 4 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 μg/mL), and carbenicillin (100 μg/mL). The following day, each culture was inoculated into 50 mL of fresh medium with 0.7% $CaCO_3$ and grown for 48 hours at 37° C., at which point the culturing temperature was increased to 65° C. The cells were cultured for an additional 24 hours, after which the concentrations of lysine and cadaverine in each culture were determined (Table 4).

TABLE 4

Production of lysine and cadaverine by *E. coli* strains containing Synthetic Operons I and II, and co-producing lysine decarboxylases at 65° C.

| Plasmids | Protein(s) | Lysine (g/L) | Cadaverine (g/L) |
|---|---|---|---|
| pCIB103-3 | S-LysC, DapA, LysA, Asd, DapB, AspC, TetA | 6.0 ± 0.1 | N.D. |
| pCIB103-3, pCIB71 | S-LysC, DapA, LysA, Asd, DapB, AspC, TetA, CadA | 0.2 ± 0.1 | 5.5 ± 0.3 |
| pCIB103-3, pCIB370 | S-LysC, DapA, LysA, Asd, DapB, AspC, TetA, TsLDC | 0.4 ± 0.2 | 5.9 ± 0.2 |
| pCIB103-3, pCIB371 | S-LysC, DapA, LysA, Asd, DapB, AspC, TetA, GkLDC | 0.3 ± 0.2 | 6.0 ± 0.3 |
| pCIB103-3, pCIB372 | S-LysC, DapA, LysA, Asd, DapB, AspC, TetA, TeLDC | 0.3 ± 0.1 | 5.8 ± 0.2 |
| pCIB103-3, pCIB373 | S-LysC, DapA, LysA, Asd, DapB, AspC, TetA, TrLDC | 0.2 ± 0.1 | 6.0 ± 0.1 |

As shown in Table 4, the incubation of the host cells at 65° C. during the final 24 hours of the fermentation led to no significant change in lysine or cadaverine production when no lysine decarboxylase was overexpressed (pCIB103-3), or when the mesophilic CadA was overexpressed. However, overexpression of the thermophilic lysine decarboxylases (pCIB103-3, pCIB370-373) led to the accumulation of cadaverine instead of lysine in the fermentation media after the host cells were incubated at 65° C. for a period of time.

Table of plasmids used in Examples

| Host | Protein(s) Overexpressed | Plasmid |
|---|---|---|
| | CadA | pCIB71 |
| | CadA, Cat | pCIB128 |
| | TsLDC | pCIB370 |
| | GkLDC | pCIB371 |
| | TeLDC | pCIB372 |
| | TrLDC | pCIB373 |
| | S-LysC, DapA, LysA, Asd, DapB, AspC, TetA | pCIB103-3 |
| *E. coli* | CadA | pCIB71 |
| *E. coli* | TsLDC | pCIB370 |
| *E. coli* | GkLDC | pCIB371 |
| *E. coli* | TeLDC | pCIB372 |
| *E. coli* | TrLDC | pCIB373 |
| *E. coli* | S-LysC, DapA, LysA, Asd, DapB, AspC, TetA | pCIB103-3 |
| *E. coli* | S-LysC, DapA, LysA, Asd, DapB, AspC, TetA, CadA | pCIB103-3, pCIB71 |
| *E. coli* | S-LysC, DapA, LysA, Asd, DapB, AspC, TetA, TsLDC | pCIB103-3, pCIB370 |
| *E. coli* | S-LysC, DapA, LysA, Asd, DapB, AspC, TetA, GkLDC | pCIB103-3, pCIB371 |
| *E. coli* | S-LysC, DapA, LysA, Asd, DapB, AspC, TetA, TeLDC | pCIB103-3, pCIB372 |
| *E. coli* | S-LysC, DapA, LysA, Asd, DapB, AspC, TetA, TrLDC | pCIB103-3, pCIB373 |

Table of primer sequences used in Examples.

| Name | Sequence (5'-3') |
|---|---|
| cadA-F (SEQ ID NO: 11) | ggcgagctcacacaggaaacagaccatgaacgttat tgcaatattgaatcac |
| cadA-R (SEQ ID NO: 12) | ggctctagaccacttcccttgtacgagc |
| cadA-F2 (SEQ ID NO: 13) | atttcacacaggaaacagctatgaacgttattgcaa tattgaat |
| cadA-R2 (SEQ ID NO: 14) | agctgtttcctgtgtgaaat |
| cat-HindIII-F (SEQ ID NO: 15) | ggcaagcttgagaaaaaaatcactggatatacc |
| cat-NdeI-R (SEQ ID NO: 16) | ggccatatgtaagggcaccaataactgcc |
| TsLDC-SacI-F (SEQ ID NO: 17) | ggcgagctcatggagaagcaagagattaacaag |
| TsLDC-XbaI-R (SEQ ID NO: 18) | ggctctagattagaaatcggttacaacctgaatg |
| TsLDC-F (SEQ ID NO: 19) | atttcacacaggaaacagctatggagaagcaagag attaacaag |
| GkLDC-SacI-F (SEQ ID NO: 20) | ggcgagctcatgtctcagctcgagacccctc |
| GkLDC-XbaI-R (SEQ ID NO: 21) | ggctctagattaacgaattggtttgtattctttaa tgac |
| GkLDC-F (SEQ ID NO: 22) | atttcacacaggaaacagctatgtctcagctcgag accccctc |
| TeLDC-SacI-F (SEQ ID NO: 23) | ggcgagctcatggaacctctgctgcgtgc |
| TeLDC-XbaI-R (SEQ ID NO: 24) | ggctctagattaaactttgcagatacgcagag |

-continued

| Table of primer sequences used in Examples. | |
|---|---|
| Name | Sequence (5'-3') |
| TeLDC-F (SEQ ID NO: 25) | atttcacacaggaaacagctatggaacctctgctg cgtgc |
| TrLDC-SacI-F (SEQ ID NO: 26) | ggcgagctcatgtctgaagaacagcaacg |
| TrLDC-XbaI-R (SEQ ID NO: 27) | ggctctagattaggcacgaacgacacgga |
| TrLDC-F (SEQ ID NO: 28) | atttcacacaggaaacagctatgtctgaagaacag caacg |

Illustrative Nucleic Acid an Polypeptide Sequences:

*T. syntrophicus* lysine decarboxylase polypeptide sequence--
underlined residues are representative conserved or semi-
conserved residues compared to CadA
SEQ ID NO: 1
MEKQEINKFSKTPLIQALKEYEKKDSLRFHMPGHKGRCPKGVFCDIKENLFGWDVTEIPG

LDDFAQPEGPIKEAQEKLSALYGADTSYFLVNGATSGIISMMAGALSEKDKILIPRTSHKS

VLSGLILTGASAAYIMPERCEELGVYAQVEPCAITNKLIENPDIKAILVTNPVYQGFCPDIA

RVAEIAKERGTTLLADEAQGPHFGFSKKVPQSAGKFADAWVQSPHKMLTSLTQSAWLHI

KGNRIDKERLEDFLHIVTTSSPSYILMASLDGTRELIEENGNSYIEKAVELAQKARYEINNS

TVFYAPGQEILGKYGISSQDPLHLMVNVSCAGYTGYDIEKALREDFSIYAEYADLCNVYF

LITFSNTLEDIKGLLAVLSHFKPLKNKVKPCFWIKDLPKVALEPKKAFKLPAKSVPFKDSA

GSVSKRPLVPYPPGAPLVMPGEIIEKEHIEMINEILNSGGYCQGVTSEKFIQVVTDF

*G. kaustophilus* lysine decarboxylase polypeptide sequence--
underlined residues are representative conserved or semi-
conserved residues compared to CadA
SEQ ID NO: 2
MSQLETPLFTGLLEHMKKNPVQFHIPGHKKGAGMDPEFRAFIGDNALAIDLINISPLDDL

HHPKGMIKRAQELAAEAFGADYTFFSVQGTSGAIMTMVMSVAGPGDKIIVPRNVHKSV

MSAIVFSGATPIFIHPEIDKELGISHGITPQAVEKALRQHPDAKGVLVINPTYFGIAGDLKKI

VDIAHSYNVPVLVDEAHGVHIHFHEDLPLSAMQAGADMAATSVHKLGGSLTQSSILNVR

EGLVSAKHVQAILSMLTTTSTSYLLLASLDVARKQLATKGRELIDKAIRLADWTRRQINE

IPYLYCVGEEILGTEATYDYDPTKLIISVKELGLTGHDVERWLRETYNIEVELSDLYNILCI

ITPGDTEREASLLVEALRRLSKQFSHQAEKGIKPKVLLPDIPALALTPRDAFYAETEVVPF

HESAGRIIAEFVMVYPPGIPIFIPGEIITEENLKYIETNLAAGLPVQGPEDDTLQTLRVIKEY

KPIR

*T. elongates* lysine decarboxylase polypeptide sequence--
underlined residues are representative conserved or semi-
conserved residues compared to CadA
SEQ ID NO: 3
MEPLLRALWGTALEQDLSELPGLDNLAQPTGVLAEAQAVVAATVGSDRAWFLVNGAT

GGLLAALLATVGPGDRVLVGRNVHRSVIAGLVLAGAKPVYLGVGVDPQWGLPWPVTR

DVVAAGLAAYPDTKAVVLVSPTYEGLCSPLLEIAQCVHNHGVPLIVDEAHGSHFAYHPA

FPVTALAAGADVVVQSWHKTLGTLTQTAVLHLKGERVSAERLSQALNLVQTSSPNYWL

LAALEGAGVQMAQQGEQIYGRLLQWVKTFEWPLPRWQPPGIPQDPLRLTLGTWPIGLT

GFALDELLQPQIIAEFPSGRSLTFCLGLGTTQTMLETLADRLKSVYTEYCHNAPLPPLAIPS

-continued
IPSCQEPALSPREAYFCPQRSIPLRAALNEISAETIAPYPPGIPTVIAGERFTESVIATLQTLQ

ELGAEMVGASDPTLQTLRICKV

T. roseum lysine decarboxylase polypeptide sequence--T.
elongates lysine decarboxylase polypeptide sequence--
underlined residues are representative conserved or
semi-conserved residues compared to CadA
SEQ ID NO: 4
MSEEQQRAPYLEQWLAYVDECVIPFTTPGHKQGRGAPPEFVAAFGERALALDIPHDGGT

FDAHLEHDPLVAAERLAAALWGARDAVFLVNGSTTGNLAALLTLGRPGQPIVVTRAMH

KSLLAGLVLSGARPVYVVPAVHPESGILLDLPPESVAQALAAWPDATAVALVSPTYTGV

TSDTAELAALCHAHGVPLFVDEAWGPHLPFHPALPAAAIPSGADLAVTSLHKLAGSLTQ

TALLLMAGNLVDQAQLRAATAMVQTTSPAAFLYASLDAARRRLALEGEQLLARTLELA

EHARRELAAIPGLEVVGPEIVAGRPGAGFDRTRLVVDVQGFGLTGLEVKRILRRDFRIAA

EMADLVSVVFLITIGDTPETIAALVAAFRALAADRTRPDCAAGRRAVRALLRSTGPIVAG

APQAMTPREAFFAPAERVPLADAVGRVAAEPVTPYPPGIPVLAPGEVVRPEVVEFLQAG

RAAGMRFNGASDPTLATLRVVRA

T. syntrophicus lysine decarboxylase codon-optimized nucleic
acid sequence
SEQ ID NO: 5
ATGGAGAAGCAAGAGATTAACAAGTTCTCTAAGACCCCGCTCATCCAAGCGCTGAA

AGAATACGAGAAAAGGATTCTCTGCGTTTCCACATGCCAGGTCACAAAGGCCGTTG

TCCAAAAGGTGTTTTTTGCGATATTAAGGAGAACCTGTTCGGTTGGGATGTTACCGA

AATCCCGGGTCTGGATGACTTCGCTCAACCGGAAGGTCCGATCAAGGAAGCACAGG

AGAAACTGTCTGCGCTGTACGGTGCCGACACCTCCTATTTCCTCGTTAATGGTGCAAC

CTCTGGTATCATTTCTATGATGGCGGGTGCTCTGTCCGAAAAGGACAAAATCCTGAT

CCCGCGTACCAGCCATAAGAGCGTACTCTCTGGTCTGATTCTCACTGGCGCCTCTGCG

GCGTACATCATGCCGGAGCGTTGCGAAGAGCTGGGTGTTTACGCACAGGTGGAACCT

TGTGCCATCACCAACAAACTGATCGAGAACCCGGATATCAAAGCGATTCTGGTTACC

AACCCAGTGTACCAGGGTTTCTGCCCGGACATCGCGCGTGTTGCGGAAATCGCGAAA

GAACGCGGTACCACCCTGCTCGCAGACGAAGCGCAAGGCCCACATTTCGGCTTTTCC

AAGAAAGTTCCGCAGTCTGCGGGTAAGTTCGCGGATGCGTGGGTTCAGTCCCCTCAC

AAAATGCTGACGAGCCTGACCCAATCTGCGTGGCTGCACATCAAGGGCAATCGTATC

GACAAGGAACGTCTGGAAGACTTTCTCCACATCGTTACCACCTCTTCTCCGTCTTACA

TCCTCATGGCGTCTCTGGACGGTACCCGCGAGCTGATTGAAGAAAACGGTAACTCCT

ACATTGAAAAGGCGGTTGAACTGGCTCAGAAAGCGCGTTATGAAATCAACAACTCT

ACTGTTTTCTACGCGCCAGGCCAGGAGATTCTCGGTAAATACGGTATTTCTTCTCAGG

ACCCGCTGCATCTGATGGTTAATGTTTCTTGCGCGGGTTACACGGGCTACGACATCG

AAAAAGCCCTGCGTGAGGACTTTTCTATCTACGCCGAATACGCGGACCTGTGTAACG

TTTACTTCCTCATTACGTTTAGCAATACCCTGGAGGACATTAAAGGTCTCCTCGCGGT

TCTGTCTCACTTCAAACCGCTCAAAAACAAAGTTAAACCGTGCTTCTGGATCAAAGA

CCTGCCGAAAGTTGCGCTGGAGCCAAAGAAGGCGTTCAAACTGCCGGCGAAATCTG

TGCCTTTCAAAGATTCTGCTGGTAGCGTTTCTAAACGCCCGCTGGTTCCGTATCCGCC

AGGTGCGCCACTCGTGATGCCGGGTGAGATCATTGAGAAAGAGCACATCGAGATGA

TTAATGAAATTCTCAACTCTGGCGGCTACTGCCAGGGTGTTACGTCTGAAAAGTTCA

TTCAGGTTGTAACCGATTTCTAA

*G. kaustophilus* lysine decarboxylase codon-optimized nucleic acid sequence

SEQ ID NO: 6

ATGTCTCAGCTCGAGACCCCTCTGTTCACCGGTCTGCTCGAACACATGAAGAAAAAC

CCGGTCCAGTTTCACATTCCAGGTCACAAGAAAGGTGCTGGTATGGACCCTGAGTTC

CGTGCGTTTATCGGTGATAACGCGCTCGCGATCGACCTGATCAACATCTCCCCTCTCG

ACGACCTCCACCACCCGAAAGGCATGATCAAACGTGCGCAGGAACTGGCTGCGGAA

GCGTTTGGCGCGGACTACACGTTCTTCAGCGTTCAAGGCACCAGCGGTGCCATCATG

ACGATGGTAATGTCTGTTGCGGGTCCGGGCGATAAGATCATCGTCCCTCGTAACGTT

CACAAATCTGTTATGTCTGCCATCGTTTTCTCTGGCGCGACCCCTATTTTCATCCACC

CGGAAATCGATAAGGAGCTGGGTATTAGCCACGGTATTACCCCGCAGGCCGTGGAG

AAAGCCCTGCGTCAACACCCTGATGCTAAAGGCGTTCTGGTAATCAACCCGACTTAT

TTCGGTATCGCGGGTGACCTCAAAAAGATCGTTGACATCGCGCACTCTTATAATGTG

CCGGTCCTGGTAGATGAAGCGCACGGTGTTCATATTCACTTCCACGAGGACCTCCCA

CTCAGCGCAATGCAGGCGGGTGCGGATATGGCGGCGACGTCCGTGCACAAGCTGGG

CGGTAGCCTGACTCAGTCTTCCATTCTGAACGTACGCGAAGGTCTGGTTTCTGCTAAA

CACGTGCAAGCGATTCTCTCTATGCTGACCACCACTTCTACCTCTTATCTGCTGCTGG

CTTCCCTGGACGTAGCGCGTAAACAGCTGGCAACCAAAGGTCGTGAACTCATCGACA

AAGCCATCCGCCTCGCGGATTGGACCCGTCGCCAGATTAACGAGATCCCGTACCTCT

ACTGCGTGGGTAAGAGATCCTGGGTACCGAAGCAACCTACGACTACGATCCGACT

AAACTGATCATCAGCGTAAAAGAACTCGGTCTCACTGGCCATGACGTTGAGCGTTGG

CTCCGTGAAACCTACAATATCGAAGTTGAACTGTCTGACCTCTATAACATCCTCTGCA

TCATCACCCCGGGTGATACTGAGCGCGAAGCGTCTCTCCTGGTGGAAGCACTGCGCC

GTCTGTCTAAACAATTCTCCCATCAGGCCGAAAAGGGTATCAAACCTAAGGTTCTCC

TGCCGGATATTCCTGCCCTCGCCCTGACGCCTCGTGACGCGTTCTATGCGGAAACCG

AAGTCGTTCCGTTCCATGAGTCCGCCGGTCGTATCATCGCGGAGTTTGTAATGGTTTA

CCCACCGGGCATCCCAATCTTCATCCCTGGCGAGATTATCACTGAGGAAAACCTGAA

ATACATCGAAACCAACCTGGCGGCTGGCCTCCCGGTTCAGGGCCCAGAAGACGACA

CGCTGCAGACCCTCCGTGTCATTAAAGAATACAAACCAATTCGTTAA

*T. elongates* lysine decarboxylase codon-optimized nucleic acid sequence

SEQ ID NO: 7

ATGGAACCTCTGCTGCGTGCGCTGTGGGGTACTGCACTCGAACAAGACCTGTCTGAG

CTGCCGGGTCTCGATAACCTGGCGCAACCGACCGGTGTTCTCGCAGAAGCGCAGGCT

GTTGTTGCGGCAACTGTAGGTTCTGACCGTGCGTGGTTTCTGGTTAATGGTGCAACG

GGCGGTCTCCTCGCCGCACTCCTGGCCACCGTAGGTCCTGGTGATCGTGTGCTGGTTG

GCCGTAATGTTCACCGTTCTGTTATCGCAGGTCTCGTTCTGGCAGGTGCAAAGCCGGT

TTACCTGGGTGTTGGTGTAGATCCGCAATGGGTCTGCCGTGGCCGGTAACTCGTGA

TGTGGTAGCCGCTGGTCTGGCCGCATATCCGGACACCAAAGCGGTTGTGCTCGTTTC

TCCGACGTATGAAGGCCTGTGCAGCCCACTGCTGGAGATCGCGCAATGCGTTCACAA

CCACGGTGTCCCGCTGATCGTTGACGAAGCACATGGTTCTCACTTCGCGTATCACCC

AGCTTTCCCGGTGACGCGCTCGCTGCTGGCGCTGACGTTGTCGTACAGTCTTGGCAT

AAAACCCTGGGTACGCTGACCCAGACGGCGGTTCTCCACCTCAAAGGTGAGCGTGTT

```
TCCGCCGAACGTCTGTCTCAGGCTCTGAACCTGGTTCAAACCTCTTCCCCGAACTACT

GGCTGCTCGCAGCACTGGAAGGTGCAGGCGTCCAAATGGCTCAGCAGGGTGAGCAG

ATTTACGGTCGCCTGCTCCAGTGGGTAAAGACCTTCGAATGGCCACTCCCGCGTTGG

CAGCCGCCTGGCATCCCTCAGGACCCTCTCCGTCTCACTCTGGGCACTTGGCCTATTG

GTCTGACGGGTTTCGCGCTCGACGAACTCCTCCAGCCGCAGATCATCGCGGAGTTCC

CGTCCGGTCGTTCCCTCACGTTTTGCCTCGGTCTCGGTACCACCCAAACCATGCTCGA

AACGCTGGCGGACCGCCTGAAATCTGTTTACACCGAATACTGCCACAACGCCCCTCT

GCCTCCTCTCGCGATTCCATCTATCCCGTCTTGCCAGGAACCTGCTCTCAGCCCGCGT

GAAGCGTACTTCTGCCCGCAGCGCTCTATTCCGCTCCGCGCAGCTCTCAACGAAATC

TCTGCGGAGACCATCGCGCCGTATCCACCGGGTATCCCGACCGTGATCGCGGGTGAA

CGTTTCACGGAATCTGTCATCGCAACCCTCCAGACCCTGCAAGAACTCGGTGCAGAA

ATGGTCGGTGCGAGCGACCCTACGCTGCAGACTCTGCGTATCTGCAAAGTTTAA
```

*T. roseum* lysine decarboxylase codon-optimized nucleic acid sequence

SEQ ID NO: 8

ATGTCTGAAGAACAGCAACGTGCTCCGTACCTGGAGCAATGGCTGGCGTACGTTGAC

GAGTGCGTTATCCCGTTTACCACTCCGGGTCACAAACAAGGTCGCGGTGCGCCACCG

GAGTTCGTTGCGGCGTTCGGTGAACGTGCGCTCGCTCTGGACATTCCGCATGACGGT

GGCACCTTTGACGCGCATCTGGAACATGACCCGCTCGTTGCCGCCGAACGTCTGGCT

GCCGCACTGTGGGGTGCACGCGATGCGGTGTTTCTGGTTAACGGTTCCACCACTGGT

AACCTGGCGGCTCTGCTCACTCTCGGTCGCCCAGGTCAGCCGATTGTTGTTACTCGTG

CCATGCATAAGAGCCTGCTGGCAGGTCTGGTCCTGAGCGGTGCTCGCCCTGTCTACG

TTGTACCGGCCGTACACCCAGAATCCGGTATCCTCCTCGATCTCCCTCCGGAATCTGT

TGCGCAGGCGCTGGCCGCGTGGCCTGATGCGACGGCTGTAGCTCTGGTGTCCCCGAC

CTACACTGGCGTTACCTCTGACACTGCTGAACTGGCAGCCCTCTGTCACGCTCATGGT

GTTCCACTGTTTGTTGATGAAGCGTGGGGTCCGCACCTCCCGTTCCATCCAGCACTCC

CAGCAGCAGCTATTCCGTCTGGTGCCGATCTGGCGGTTACTTCTCTGCACAAACTGG

CGGGTTCCCTCACCCAAACCGCTCTCCTCCTGATGGCAGGCAACCTCGTAGACCAAG

CCCAGCTGCGTGCAGCCACGGCAATGGTGCAAACCACCAGCCCTGCAGCCTTCCTGT

ACGCGTCCCTGGATGCTGCCCGTCGCCGTCTCGCGCTCGAAGGTGAACAGCTCCTCG

CACGTACTCTCGAGCTGGCTGAGCACGCTCGCCGTGAACTCGCCGCCATCCCGGGTC

TGGAGGTGGTCGGTCCAGAAATTGTTGCGGGTCGTCCGGGTGCCGGCTTCGATCGTA

CTCGCCTCGTTGTTGACGTTCAGGGTTTCGGTCTGACTGGCCTCGAAGTAAAGCGTAT

CCTGCGTCGTGACTTCCGTATTGCAGCTGAAATGGCAGATCTCGTCTCTGTTGTTTTC

CTCATCACCATCGGTGACACCCCAGAGACCATCGCTGCCCTGGTAGCAGCTTTCCGT

GCACTCGCTGCTGACCGTACCCGTCCAGACTGTGCTGCCGGTCGTCGTGCAGTACGC

GCCCTCCTCCGTTCTACCGGTCCGATCGTCGCGGGTGCTCCTCAGGCGATGACCCCGC

GTGAAGCTTTCTTCGCTCCAGCTGAGCGCGTTCCGCTCGCGGATGCCGTCGGTCGTGT

TGCAGCCGAGCCGGTTACCCCATATCCGCCTGGTATTCCGGTACTGGCCCCAGGTGA

AGTGGTTCGCCCGGAGGTAGTTGAATTCCTCCAGGCAGGCCGTGCCGCTGGTATGCG

TTTCAATGGCGCGTCTGACCCGACTCTGGCGACCCTCCGTGTCGTTCGTGCCTAA

-continued

SEQ ID NO: 9
CadA polypeptide sequence
MNVIAILNHMGVYFKEEPIRELHRALERLNFQIVYPNDRDDLLKLIENNARLCGVIFDWD

KYNLELCEEISKMNENLPLYAFANTYSTLDVSLNDLRLQISFFEYALGAAEDIANKIKQTT

DEYINTILPPLTKALFKYVREGKYTFCTPGHMGGTAFQKSPVGSLFYDFFGPNTMKSDISI

SVSELGSLLDHSGPHKEAEQYIARVFNADRSYMVTNGTSTANKIVGMYSAPAGSTILIDR

NCHKSLTHLMMMSDVTPIYFRPTRNAYGILGGIPQSEFQHATIAKRVKETPNATWPVHA

VITNSTYDGLLYNTDFIKKTLDVKSIHFDSAWVPYTNFSPIYEGKCGMSGGRVEGKVIYE

TQSTHKLLAAFSQASMIHVKGDVNEETFNEAYMMHTTTSPHYGIVASTETAAAMMKGN

AGKRLINGSIERAIKFRKEIKRLRTESDGWFFDVWQPDHIDTTECWPLRSDSTWHGFKNI

DNEHMYLDPIKVTLLTPGMEKDGTMSDFGIPASIVAKYLDEHGIVVEKTGPYNLLFLFSI

GIDKTKALSLLRALTDFKRAFDLNLRVKNMLPSLYREDPEFYENMRIQELAQNIHKLIVH

HNLPDLMYRAFEVLPTMVMTPYAAFQKELHGMTEEVYLDEMVGRINANMILPYPPGVP

LVMPGEMITEESRPVLEFLQMLCEIGAHYPGFETDIHGAYRQADGRYTVKVLKEESKK

SEQ ID NO: 10
Escherichia coli cadA nucleic acid sequence
ATGAACGTTATTGCAATATTGAATCACATGGGGGTTTATTTTAAAGAAGAACCCATC

CGTGAACTTCATCGCGCGCTTGAACGTCTGAACTTCCAGATTGTTTACCCGAACGAC

CGTGACGACTTATTAAAACTGATCGAAAACAATGCGCGTCTGTGCGGCGTTATTTTT

GACTGGGATAAATATAATCTCGAGCTGTGCGAAGAAATTAGCAAAATGAACGAGAA

CCTGCCGTTGTACGCGTTCGCTAATACGTATTCCACTCTCGATGTAAGCCTGAATGAC

CTGCGTTTACAGATTAGCTTCTTTGAATATGCGCTGGGTGCTGCTGAAGATATTGCTA

ATAAGATCAAGCAGACCACTGACGAATATATCAACACTATTCTGCCTCCGCTGACTA

AAGCACTGTTTAAATATGTTCGTGAAGGTAAATATACTTTCTGTACTCCTGGTCACAT

GGGCGGTACTGCATTCCAGAAAAGCCCGGTAGGTAGCCTGTTCTATGATTTCTTTGG

TCCGAATACCATGAAATCTGATATTTCCATTTCAGTATCTGAACTGGGTTCTCTGCTG

GATCACAGTGGTCCACACAAAGAAGCAGAACAGTATATCGCTCGCGTCTTTAACGCA

GACCGCAGCTACATGGTGACCAACGGTACTTCCACTGCGAACAAAATTGTTGGTATG

TACTCTGCTCCAGCAGGCAGCACCATTCTGATTGACCGTAACTGCCACAAATCGCTG

ACCCACCTGATGATGATGAGCGATGTTACGCCAATCTATTTCCGCCCGACCCGTAAC

GCTTACGGTATTCTTGGTGGTATCCCACAGAGTGAATTCCAGCACGCTACCATTGCTA

AGCGCGTGAAAGAAACACCAAACGCAACCTGGCCGGTACATGCTGTAATTACCAAC

TCTACCTATGATGGTCTGCTGTACAACACCGACTTCATCAAGAAAACACTGGATGTG

AAATCCATCCACTTTGACTCCGCGTGGGTGCCTTACACCAACTTCTCACCGATTTACG

AAGGTAAATGCGGTATGAGCGGTGGCCGTGTAGAAGGGAAAGTGATTTACGAAACC

CAGTCCACTCACAAACTGCTGGCGGCGTTCTCTCAGGCTTCCATGATCCACGTTAAA

GGTGACGTAAACGAAGAAACCTTTAACGAAGCCTACATGATGCACACCACCACTTCT

CCGCACTACGGTATCGTGGCGTCCACTGAAACCGCTGCGGCGATGATGAAAGGCAAT

GCAGGTAAGCGTCTGATCAACGGTTCTATTGAACGTGCGATCAAATTCCGTAAAGAG

ATCAAACGTCTGAGAACGGAATCTGATGGCTGGTTCTTTGATGTATGGCAGCCGGAT

CATATCGATACGACTGAATGCTGGCCGCTGCGTTCTGACAGCACCTGGCACGGCTTC

AAAAACATCGATAACGAGCACATGTATCTTGACCCGATCAAAGTCACCCTGCTGACT

-continued

```
CCGGGGATGGAAAAAGACGGCACCATGAGCGACTTTGGTATTCCGGCCAGCATCGT

GGCGAAATACCTCGACGAACATGGCATCGTTGTTGAGAAAACCGGTCCGTATAACCT

GCTGTTCCTGTTCAGCATCGGTATCGATAAGACCAAAGCACTGAGCCTGCTGCGTGC

TCTGACTGACTTTAAACGTGCGTTCGACCTGAACCTGCGTGTGAAAAACATGCTGCC

GTCTCTGTATCGTGAAGATCCTGAATTCTATGAAAACATGCGTATTCAGGAACTGGC

TCAGAATATCCACAAACTGATTGTTCACCACAATCTGCCGGATCTGATGTATCGCGC

ATTTGAAGTGCTGCCGACGATGGTAATGACTCCGTATGCTGCATTCCAGAAAGAGCT

GCACGGTATGACCGAAGAAGTTTACCTCGACGAAATGGTAGGTCGTATTAACGCCAA

TATGATCCTTCCGTACCCGCCGGGAGTTCCTCTGGTAATGCCGGGTGAAATGATCAC

CGAAGAAAGCCGTCCGGTTCTGGAGTTCCTGCAGATGCTGTGTGAAATCGGCGCTCA

CTATCCGGGCTTTGAAACCGATATTCACGGTGCATACCGTCAGGCTGATGGCCGCTA

TACCGTTAAGGTATTGAAAGAAGAAAGCAAAAATAA
```

What is claimed is:

1. A method of producing cadaverine, the method comprising:
   (a) culturing a mesophilic microorganism host cell at a temperature from 20° C. to 50° C. for a time period sufficient to accumulate lysine, wherein the mesophilic microorganism host cell produces lysine and is genetically modified to express a thermophilic lysine decarboxylase and to overexpress one or more lysine biosynthesis polypeptides, and wherein the amino acid sequence of the thermophilic lysine decarboxylase has at least 95% amino acid sequence identity to any one of SEQ ID NOS: 1-4; and
   (b) following step (a), incubating the culture of (a) at a temperature of above 55° C. and less than 110° C. to thereby produce cadaverine.

2. The method of claim 1, wherein step (a) is performed at a temperature of from 25° C. to 45° C.

3. The method of claim 1, wherein step (a) is performed at a temperature of from 30° C. to 40° C.

4. The method of claim 1, wherein step (a) is performed at a temperature of from 35° C. to 39° C.

5. The method of claim 1, wherein step (b) is performed at a temperature of from 55° C. to 90° C.

6. The method of claim 1, wherein step (b) is performed at a temperature of from 60° C. to 75° C.

7. The method of claim 1, wherein step (b) is performed at a temperature of from 60° C. to 70° C.

8. The method of claim 1, wherein the thermophilic lysine decarboxylase comprises the amino acid sequence of any one of SEQ ID NOS: 1-4.

* * * * *